(12) United States Patent
Raichle et al.

(10) Patent No.: US 8,546,293 B2
(45) Date of Patent: Oct. 1, 2013

(54) PROCESS FOR CONTINUOUSLY PRODUCING GEOMETRIC SHAPED CATALYST BODIES K

(75) Inventors: Andreas Raichle, Dresden (DE); Holger Borchert, Offstein (DE); Klaus Joachim Mueller-Engel, Stutensee (DE); Catharina Horstmann, Ludwigshafen (DE); Josef Macht, Weiden (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 13/607,962

(22) Filed: Sep. 10, 2012

(65) Prior Publication Data
US 2013/0006009 A1 Jan. 3, 2013

Related U.S. Application Data

(62) Division of application No. 12/634,149, filed on Dec. 9, 2009.

(60) Provisional application No. 61/122,129, filed on Dec. 12, 2008.

(30) Foreign Application Priority Data

Dec. 12, 2008 (DE) .......................... 10 2008 054 586

(51) Int. Cl.
*B01J 27/24* (2006.01)

(52) U.S. Cl.
USPC ........... 502/200; 502/174; 502/201; 264/109; 562/532; 562/535; 558/426

(58) Field of Classification Search
USPC ......... 502/200, 174, 201; 264/109; 424/489; 558/426; 568/479; 562/532, 535
See application file for complete search history.

(56) References Cited

U.S. PATENT DOCUMENTS

| | | | |
|---|---|---|---|
| 6,333,293 B1 | 12/2001 | Kase et al. | |
| 7,129,195 B2 | 10/2006 | Felder et al. | |
| 7,147,011 B2 | 12/2006 | Tazawa et al. | |
| 2004/0034249 A1 | 2/2004 | Arnold et al. | |
| 2005/0131253 A1 | 6/2005 | Teshigahara et al. | |
| 2005/0161373 A1 | 7/2005 | Tazawa et al. | |
| 2005/0263926 A1 | 12/2005 | Tazawa et al. | |
| 2008/0111269 A1 | 5/2008 | Politi et al. | |
| 2008/0177105 A1 | 7/2008 | Raichle et al. | |
| 2008/0312477 A1 | 12/2008 | Raichle et al. | |
| 2009/0171117 A1 | 7/2009 | Arnold et al. | |

FOREIGN PATENT DOCUMENTS

| | | |
|---|---|---|
| DE | 1117245 | 11/1961 |
| DE | 24 35 860 | 2/1976 |
| DE | 198 35 247 A1 | 2/1999 |
| DE | 198 55 913 A1 | 6/2000 |
| DE | 199 22 113 A1 | 8/2000 |
| DE | 199 10 506 A1 | 9/2000 |
| DE | 199 48 241 A1 | 4/2001 |
| DE | 199 48 248 A1 | 4/2001 |
| DE | 199 48 523 A1 | 4/2001 |
| DE | 199 27 624 A1 | 12/2001 |
| DE | 100 46 672 A1 | 3/2002 |
| DE | 100 46 957 A1 | 4/2002 |
| DE | 100 51 419 A1 | 4/2002 |
| DE | 103 13 209 A1 | 3/2004 |
| DE | 103 13 213 A1 | 10/2004 |
| DE | 103 60 369 A1 | 7/2005 |
| DE | 10 2005 013 039 A1 | 9/2006 |
| DE | 10 2007 003 778.5 | 1/2007 |
| DE | 10 2005 035 978 A1 | 2/2007 |
| DE | 10 2005 037 678 A1 | 2/2007 |
| DE | 10 2004 003 212 B4 | 12/2007 |
| DE | 10 2007 004 961 A1 | 7/2008 |
| DE | 10 2007 025 869 A1 | 7/2008 |
| DE | 10 2007 017 080 A1 | 10/2008 |
| DE | 10 2007 028 332 A1 | 12/2008 |
| DE | 10 2008 040 093 A1 | 12/2008 |
| DE | 10 2008 040 094 A1 | 1/2009 |
| DE | 10 2008 042 060 A1 | 6/2009 |
| DE | 10 2008 042 061 A1 | 3/2010 |
| DE | 10 2008 042 064 A1 | 3/2010 |
| EP | 0 184 790 A2 | 6/1986 |
| EP | 0 467 144 A1 | 1/1992 |
| EP | 0 700 714 A1 | 3/1996 |
| EP | 1 060 792 A1 | 12/2000 |
| WO | 02/062737 A2 | 8/2002 |
| WO | 03/078059 A1 | 9/2003 |
| WO | 03/078310 A2 | 9/2003 |
| WO | 2005/030393 A1 | 4/2005 |
| WO | 2005/049200 A1 | 6/2005 |
| WO | 2007/017431 A1 | 2/2007 |
| WO | 2008/014839 A1 | 2/2008 |
| WO | 00/53558 | 9/2000 |
| WO | 01/36364 A1 | 5/2001 |
| WO | 01/68245 A1 | 9/2001 |
| WO | 02/24620 A2 | 3/2002 |
| EP | 1 106 598 A2 | 6/2001 |
| EP | 1 726 358 A1 | 11/2006 |
| JP | 64-29097 | 1/1989 |
| WO | 00/53557 | 9/2000 |

OTHER PUBLICATIONS

Search Report issued May 4, 2011 in International Application No. PCT/EP2009/066430.
Chem.-Ing.-Tech, vol. 56, No. 12, pp. 897-907 (1984).
K. Wolff, "On perforated bottoms and their use", Aufbereitungs-Technik, No. 11, pp. 457-473 (1960).

*Primary Examiner* — Colleen Dunn
*Assistant Examiner* — Haytham Soliman
(74) *Attorney, Agent, or Firm* — Oblon, Spivak, McClelland, Maier & Neustadt, L.L.P.

(57) ABSTRACT

A process for producing geometric shaped catalyst bodies K whose active material is a multielement oxide which comprises the element Mo, the elements Bi and/or V and one or more of the elements Co, Ni, Fe, Cu and alkali metals, in which sources of the different elements are used to obtain a finely divided mixture which is coarsened to a powder by press agglomeration, the coarsened powder is used to form, by press agglomeration, shaped bodies V which are separated into undamaged shaped bodies V⁺ and into damaged shaped bodies V⁻, the undamaged shaped bodies V⁺ are converted by thermal treatment to the shaped catalyst bodies K, and the damaged shaped bodies V⁻ are comminuted and recycled into the obtaining of the finely divided mixture.

8 Claims, No Drawings

PROCESS FOR CONTINUOUSLY PRODUCING GEOMETRIC SHAPED CATALYST BODIES K

This is a divisional application of U.S. application Ser. No. 12/634,149, filed Dec. 9, 2009, which is a 119(e) of 61/122,129 filed on Dec. 12, 2008.

BACKGROUND OF THE INVENTION

1. Field of the Invention

The present invention relates to a process for continuously producing geometric shaped catalyst bodies K, which comprise, as an active material, a multielement oxide which comprises, as elements E other than oxygen, the element Mo, at least one of the two elements Bi and V, and at least one further element from the group consisting of Co, Ni, Fe, Cu and the alkali metals, in process stages A) to E), in which

- in process stage A), with the aid of sources Q of the elements E, a finely divided mixture M is obtained with the proviso that at most 10% by weight of the total weight of the particles present in the finely divided mixture M have a particle diameter of $d^M \geq 160$ µm and the particle diameter $d_{50}^M$ of the particles of the mixture M satisfies the condition $1~\mu m \leq d_{50}^M \leq 150~\mu m$;
- in process stage B), the finely divided mixture M*, which consists either only of the finely divided mixture M or of a mixture of the finely divided mixture M and fines F which are obtained in the next process stage C) and are recycled into process stage B) continuously or batchwise from process stage C), is compacted by press agglomeration in which the maximum pressure applied is P1 to agglomerates A whose longest dimension L is $\geq 3$ mm;
- in process stage C), the agglomerates A are comminuted and the particulate material formed in the comminution is separated by sieving into a powder P whose particle diameters $d^P$ are $\leq 2$ mm and, to an extent of at least 90% by weight, based on the weight of the powder P, $\geq 160$ µm, as sieve oversize, and into fines F as sieve undersize, and the fines F are recycled continuously or batchwise into process stage B to obtain finely divided mixture M*;
- in process stage D), the powder P conducted into it or a mixture P* consisting of the powder P conducted into process stage D) and shaping assistants is used to obtain, by press agglomeration in which the maximum pressure applied is P2 and satisfies the relationship $P2 \geq 2 \cdot P1$, geometric shaped bodies V with the proviso that when the powder P is conveyed into process stage D) and when shaping assistants are mixed into the powder P, a particle diameter $d^P \geq 160$ µm is maintained overall in at least 40% by weight (preferably at least 60% by weight, more preferably at least 80% by weight, or at least 90% by weight or 100% by weight) of the particles of the powder P, based on the weight thereof; and
- in process stage E), at least a portion of the shaped bodies V is treated thermally at elevated temperature to obtain the geometric shaped catalyst bodies K.

2. Description of the Background

Processes for producing geometric shaped catalyst bodies which comprise, as an active material, a multielement oxide which comprises, as elements other than oxygen, the element Mo, at least one of the two elements Bi and V, and at least one further element from the group consisting of Co, Ni, Fe, Cu and the alkali metals are known (cf., for example, EP-A 184 790, US-A 2005/0263926 and JP-A 10/29097):

In general, this involves, with the aid of sources of the elements other than oxygen in the multielement oxide (sources=starting compounds which comprise at least one of the elements and which are either already oxides or those compounds which are converted to oxides by thermal treatment at elevated temperature, at least in the presence of molecular oxygen), producing a finely divided intimate mixture which comprises the elements other than oxygen in the multielement oxide in the required stoichiometry. Press agglomeration then forms, from the finely divided intimate mixture, geometric shaped bodies (shaped catalyst precursor bodies) of the desired geometry. Thermal treatment of the resulting shaped catalyst precursor bodies then affords the desired geometric shaped catalyst bodies therefrom.

Such geometric shaped catalyst bodies find use, for example, for charging (if appropriate diluted with inert shaped bodies) of the interior of the reaction tubes of a tube bundle reactor with a fixed catalyst bed. Such a fixed catalyst bed is suitable, inter alia, for performing heterogeneously catalyzed gas phase reactions (e.g. partial oxidations of organic compounds). Instead of a tube bundle reactor, it is also possible to charge a thermoplate reactor.

The appropriate reaction gas mixture flows through the fixed catalyst bed and the desired reaction proceeds during the residence time over the catalyst surface.

A disadvantage of shaped bodies obtained by mechanical compaction of a pulverulent aggregate is quite generally that the cohesion of the powder grains in the resulting shaped body is accomplished essentially not by intramolecular chemical conditions, but by remaining interparticulate bonds. Although particle deformations and fracturing operations in the compacting operation generally result in an increase in the interparticulate overall contact area, the magnitude of the interparticulate binding forces generated by the compaction is comparatively limited.

As a consequence, shaped catalyst precursor bodies obtained as described in some cases have damage, for example cracks, which are frequently barely perceptible visually. In a subsequent thermal treatment of such shaped precursor bodies, in the course of which gaseous compounds attributable to constituents which decompose and/or are converted chemically in the course of the thermal treatment are generally also released in the shaped catalyst precursor body, damage already present, for example crack formation, generally increases and in many cases develops to become a fracture. Catalyst fragments present in a fixed catalyst bed, however, result in compaction thereof and ultimately cause an increase in the pressure drop experienced in the reaction gas mixture as it flows through said bed.

A countermeasure which can be taken to reduce the above-described phenomenon consists, for example, in, prior to the introduction of the geometric shaped catalyst bodies K obtained into the fixed catalyst bed, sieving off the fragments formed in the course of production thereof (cf., for example, U.S. Pat. No. 7,147,011 and DE-A 10 2007 028 332). However, a disadvantage of such a procedure is that the raw material costs for an industrial scale production of shaped catalyst bodies are not inconsiderable, and therefore catalyst fragments obtained as sieve undersize (which passes through the sieve) in the course of sieving means a not inconsiderable material loss.

Furthermore, the measure of sieve removal of catalyst fragments cannot be employed when the thermal treatment of the shaped catalyst precursor bodies is undertaken actually within the reactor (for example in the reaction tube) (for example by passing appropriately heated gases through the reaction tubes charged with shaped precursor bodies).

In addition to the possible measure of sieve removal of catalyst fragments formed, another remedy which exists in principle for the above-described pressure drop problems is the possibility of taking measures which reduce the occurrence of catalyst fragments. Such measures recommended in the prior art are, for example, the additional use of shaping assistants, for example graphite, and the use of skillfully configured dies in the shaping (cf., for example, DE-A 10 2008 040 093 and DE-A 10 2008 040 094).

However, a disadvantage of these auxiliary measures is that they are incapable of remedying the problem described in an entirely satisfactory manner (the occurrence of catalyst fragments is not completely suppressed by the measures described and, moreover, it requires the use of specific shaping dies).

It was therefore an object of the present invention to provide an improved process for continuously preparing geometric shaped catalyst bodies K, which still has the disadvantages described to a reduced degree at worst.

In-depth studies have led to the result that the desired improvement can be achieved by, after process stage D) and prior to process stage E), separating the shaped bodies V obtained in process stage D) in a separation stage as process stage F) into non-intact shaped bodies V⁻ and into intact shaped bodies V⁺, and supplying essentially only the latter to process stage E). One advantage of the separation measures mentioned is that the proportion of catalyst fragments ultimately obtained can be reduced by them. More particularly, however, it is advantageous in that, in contrast to catalyst fragments, shaped bodies V⁻ removed as described can be recycled into the process for producing geometric shaped catalyst bodies K (without significantly reducing the performance of the resulting geometric shaped catalyst bodies K), and thus mean no material loss. Specifically, when the non-intact shaped bodies V⁻ are comminuted in a process stage G) to form a finely divided aggregate H whose particle diameter $d_{50}^H$ satisfies the condition 1 µm≤$d_{50}^H$≤150 µm and which comprises particles with a particle diameter $d^H$ of ≥160 µm to an extent of at most 10% by weight of its total weight, and the finely divided aggregate H is recycled continuously or batchwise to the additional incorporation into the finely divided mixture M* to be subjected to the press agglomeration while ensuring that the total content of the finely divided aggregate H in the finely divided mixture M* does not exceed a maximum value of 20% by weight.

The above content restriction is of relevance especially because the material present in the aggregate H recycled as described, in the course of the overall process, undergoes multiple compaction which does not impair the performance of the resulting shaped catalyst bodies K according to in-house studies.

While it is advantageous for the catalytic properties of the multielement oxide active material present in the shaped catalyst bodies K when the shaped bodies V are produced starting from a very finely divided mixture of comparatively homogeneous character, it is more favorable for the flow properties of the mixture to be compacted when it also comprises relatively coarse components (cf. WO 2008/014839). Appropriately in application terms, the starting materials in the production of geometric shaped catalyst bodies K are therefore comparatively finely divided starting mixtures which are subsequently coarsened by a first press agglomeration with downstream comminution at first only in order to improve their flow properties. The latter ensures, for example, reproducible filling of the die cavity ("the powder fills it like a liquid") in which the compaction to the shaped body V is then effected. Since the maximum pressure applied in the course of compaction to the shaped body V is significantly greater than that applied to coarsen the powder, no restriction in the quantitative proportion is required in the finely divided mixture M* with regard to material recycling from the powder coarsening.

BRIEF SUMMARY OF THE INVENTION

The solution provided for the inventive problem is thus a process for continuously producing geometric shaped catalyst bodies K (unsupported catalysts K) which comprise, as an active material, a multielement oxide which comprises, as elements other than oxygen, the element Mo, at least one of the two elements Bi and V, and at least one further element from the group consisting of Co, Ni, Fe, Cu and the alkali metals, in process stages A) to G), in which in process stage A), with the aid of sources Q of the elements E, a finely divided mixture M is obtained with the proviso that at most 10% by weight of the total weight of the particles present in the finely divided mixture M have a particle diameter of $d^M$≥160 µm and the particle diameter $d_{50}^M$ of the particles of the finely divided mixture M satisfies the condition 1 µm≤$d_{50}^M$≤150 µm;

in process stage B), the finely divided mixture M*, which consists either only of the finely divided mixture M or of a mixture of the finely divided mixture M and fines F which are obtained in the next process stage C) and are recycled into process stage B) continuously or batchwise from process stage C), is compacted by press agglomeration in which the maximum pressure applied is P1 to agglomerates A whose longest dimension L is ≥3 mm;

in process stage C), the agglomerates A are comminuted and the particulate material formed in the comminution is separated by sieving into a powder P whose particle diameters $d^P$ are ≤2 mm and, to an extent of at least 90% by weight (preferably to an extent of at least 95% by weight or to an extent of 100% by weight), based on the weight of the powder P, ≥160 µm, as sieve oversize, and into fines F as sieve undersize, and the fines F are recycled continuously or batchwise into process stage B to obtain finely divided mixture M*;

in process stage D), the powder P conducted into it or a mixture P* consisting of the powder P conducted into process stage D) and shaping assistants is used to obtain, by press agglomeration in which the maximum pressure applied is P2 and satisfies the relationship P2≥2·P1, geometric shaped bodies V with the proviso that when the powder P is conveyed into process stage D) and when shaping assistants are mixed into the powder P, a particle diameter $d^P$≥160 µm is maintained overall in at least 40% by weight (preferably at least 60% by weight, more preferably at least 80% by weight or at least 90% by weight or 100% by weight) of the particles of the powder P, based on the weight thereof; and in process stage E), at least a portion of the shaped bodies V is treated thermally at elevated temperature to obtain the geometric shaped catalyst bodies K, wherein prior to process stage E), the shaped bodies V obtained in process stage D) are separated in an additional separation stage as process stage F) into non-intact shaped bodies V⁻ and into intact (sound, undamaged, unbroken) shaped bodies V⁺, the shaped bodies V⁺ are fed to process stage E) and in process stage G), non-intact shaped bodies V⁻ are comminuted to form a finely divided aggregate H whose particle diameter $d_{50}^H$ satisfies the condition 1 µm≤$d_{50}^H$≤150 µm and which comprises particles having a particle diameter $d^H$≥160 µm to an extent of at most 10% by weight of its total weight, and the finely divided aggregate H is recycled continuously or batchwise to the additional incorporation into the finely divided mixture M* into process stage B) with the proviso that the content of finely divided aggregate H in the finely divided mixture M*, based on the total weight of the finely divided mixture M*, does not exceed 20% by weight (and process stages A) to G) are otherwise executed unchanged, i.e. with unchanged application of the process measures to be employed therein).

DETAILED DESCRIPTION OF THE INVENTION

The separation of the shaped bodies V in process stage F) into non-intact shaped bodies V⁻ and into intact shaped bodies V⁺ can in principle be effected by visual assessment of the shaped bodies V obtained (also referred to as "green bodies" V) and subsequent selection (rejection).

Appropriately in application terms, the separation of the shaped bodies V is, however, undertaken by a sieve separation. In the course of such sieving, for example, those shaped bodies V which already have crack formation or in which crack formation has already commenced (which are not "intact") generally break up. The intact shaped bodies V⁺ remain as sieve residue (also referred to as "oversize"), whereas the material which passes through the sieve (also referred to as "undersize") comprises the fragments of non-intact shaped bodies V⁻.

In principle, the shaped bodies V produced in accordance with the invention ("the sieve material") can be transported through the sieve (the term "sieve" is used in this document synonymously with the term "sieve plate"; incidentally, the term "sieve" or "sieve plate" in this document is used in the sense of the definition of the term given in EP-A 1 726 358 in column 5, lines 48 to 57) by a circular, elliptical and/or linear vibrating motion of the sieve plate. For this purpose, it is possible in principle, for a process according to the invention, to use all sieve machines recommended in, for example, Chem.-Ing.-Tech. 56 (1984) No. 12, p. 897 to 907, and in Sieben und Siebmaschinen, Grundlagen und Anwendung [Sieves and Sieving Machines, Fundamentals and Application], Wiley VCH, Paul Schmidt (2003).

A group of sieving machines which is very suitable for the inventive separation of the shaped bodies V is that of the planar sieves in which the sieving material slides as a mat of sieving material in a linear or circular manner on the sieve (the sieve plate). By virtue of its own weight and the friction against the sieve, the mat of sieving material is sheared. The very low backmixing, which usually has an adverse effect, is advantageous.

In the case of planar sieves, the vibrating motion of the sieve surface is effected in its sieve plane. The vibrating motion may be linear (back and forth) or circular (in the first case, reference is made to a linear planar vibrating sieve). In the former case, it may be in conveying direction or at right angles thereto. In the case of linear vibrating motion in conveying direction asymmetric acceleration can also bring about longitudinal transport of the sieving material in the case of a horizontal sieve.

Circular vibration offers the advantage of always maintaining optimal acceleration. It will be appreciated that, in the process according to the invention, a combination of linear and circular vibrators can also be employed.

In the case of circular vibrators, the horizontal circular motion is frequently obtained by means of a geared motor. In the case of linear vibrators, the entire sieve frame (in which the sieve plate is normally mounted in quite general terms) is made to vibrate in a linear manner by contrarotatory unbalanced masses. Linear vibrators can be employed either with a horizontal or an inclined sieve plate. In the case of an inclined sieve plate, the sieving material, by virtue of appropriate inclination of the plane of vibration relative to the sieve plate, is thrown upward and simultaneously forward in accordance with a parabolic trajectory. The angle of inclination may, for example, be from −3° to 25°. 3° to 4° are preferred in accordance with the invention. Particular preference is given in accordance with the invention, for example, to linear vibrating sieves from RHEWURM GmbH in Remscheid, Germany.

Rectangular sieving machines are preferred over round sieves for inventive planar sieving operation. In the case of the former, rectangular sieve plates are mounted in a likewise rectangular sieve frame. Frequently, the vibrating motion is configured such that the sieve residue is carried to the periphery of the sieve and discharged there.

In order to keep the sieve orifices clear in the course of inventive sieving of shaped bodies V, for example when the sieve plate is manufactured from steel with a comparatively low modulus of elasticity, it is possible to use the method of rubber ball knocking (cf. FIG. 12 in Chem.-Ing.-Tech. 56 (1984) No. 12, page 902). This involves placing rubber balls on a blank tray at a fixed distance below the sieve (the sieve plate). Even in the case of planar sieving machines, the rubber balls jump during the sieving operation (during the sieving) from below against the sieve and clean the sieve locally. Their elasticity is such that they cause essentially no additional fracture of the intact sieving material. The blank tray is usually a perforated sheet with preferably square hole orifices. In each case, the hole orifices of the blank tray are such that the material passing through the sieve can pass through.

Alternatively to rubber ball knocking, sieve cleaning during the sieving operation can also be brought about continuously by means of flat or roller brushes arranged above and/or below the sieve plate.

The selection of the particular sieve orifice for use for the inventive separation is guided by the particular geometry of the shaped bodies V. It is possible, for example, to follow the recommendations given in documents U.S. Pat. No. 7,147,011, DE-A 102 007 028 332, EP-A 1 726 358, Aufbereitungstechnik No. 11/1960, p. 457 to 473, Chem.-Ing.-Techn. 56 (1984) No. 12, p. 897 to 907, and in "Sieben und Siebmaschinen, Wiley-VCH GmbH & Co. KGaA, Paul Schmidt et al. (2003)".

In other words, the sieve plate used may, for example, be configured as a grid or grille, as a perforated or slotted sheet (i.e. as a metal sheet with punched, lasered, water-cut or milled sieve orifices), or as a sieve fabric (it consists of interwoven wires, which may be round or profiled). Grids or grilles and sieve fabric are suitable especially in the case of only one inventive kind of sieve plates having a rectangular sieve orifice. Any desired sieve orifices can be achieved in a simple manner in perforated or slotted sheets. Perforated and slotted sheets advantageous in accordance with the invention are those which have only one kind of rectangular or elongated sieve orifice. Typical sheet metal thicknesses of perforated sheet metal sieves (or slotted sheet metal sieves) useable in accordance with the invention are 1 to 5 mm, preferably 1 to 3 mm, more preferably 1 to 2 mm.

The free sieve area F (the total (cross-sectional) area of all sieve orifices present in one slotted sheet sieve plate) of slotted sheet sieve plates favorable in accordance with the invention will, based on the total area of the slotted sheet sieve plate, be typically 10 to 60%, preferably 20 to 50% and more preferably 30 to 50%.

Useful material includes especially steel (e.g. DIN materials 1.4541 or 1.4571). However, it is also possible to use rubber or plastic.

The degree of differentiation between intact and non-intact shaped bodies V is determined by the separating method employed in each case. In this document, the term "intact" should be understood in the sense of sound, undamaged or unbroken. An additional significant factor in a separation into intact shaped bodies V+ and non-intact shaped bodies V⁻ brought about by sieving is that, in the course of the sieving operation, powder dust still adhering on the shaped bodies V as a result of the production is additionally removed to a significant degree. When the aforementioned powder dust comprises ignitable constituents, for example graphite, in the case that the powder dust is not removed from the shaped bodies V, there may be undesired ignition phenomena in the course of thermal treatment thereof.

Advantageously in accordance with the invention, the process according to the invention will be performed such that the content in the finely divided mixture M* of finely divided aggregate H, based on the total weight of the finely divided mixture M*, does not exceed 15% by weight or 10% by weight. It is, however, favorable in application terms for the process according to the invention when the content in the finely divided mixture M* of finely divided aggregate H is at least temporarily, based on the total weight of the finely divided mixture M*, at least 1% by weight, or at least 3% by weight, or at least 5% by weight.

For the process according to the invention, it is also appropriate when the waste air (in the case that one or more process stages is not conducted under air but under another gas atmosphere, for example inert gas (e.g. $N_2$) or air diluted with inert gas (e.g. $CO_2$), or dried air, the term "waste air" shall also extend to these gas atmospheres) from the different process stages B) to G) is sucked out and subjected to at least one mechanical separating operation with which solid particles FP dispersed in the waste air (gas atmosphere) sucked out can be removed (this is especially true of the waste air of the apparatus used for press agglomeration in process stage B), for the waste air of the apparatus used for the press agglomeration in process stage D) and for the comminution apparatus used for the waste air in process stages C) and G), and the mixing apparatus used in process stage B) and if appropriate D)).

The solid particles FP removed, which generally originate predominantly from the finely divided materials processed in the particular process stage, can subsequently be recycled continuously or batchwise into process stage B) and likewise be incorporated into the finely divided mixture M*, with the proviso that the content in the mixture M* of such recycled solid particles FP, based on the total weight of the mixture M*, does not exceed 10% by weight, preferably 5% by weight.

The aforementioned content restriction is of relevance because the recycled solid particles FP are particularly fine and may hinder the development of the pore structure in the geometric shaped catalyst bodies K, which can ultimately result in an impairment of the catalyst performance (activity, selectivity of target product formation). The waste air may also comprise normal dust particles which can reduce the catalyst performance owing to their substance properties. According to the configuration of the recycling of the solid particles FP, of the finely divided aggregate H and of the fines F, the finely divided mixture M* in the process according to the invention may consist only of the finely divided mixture M, or of the finely divided mixture M and one or more of the aforementioned materials recycled into process stage B) (i.e. aggregate H, fines F and/or solid particles FP).

In waste air cleaning processes which employ such a mechanical separating operation and are suitable in accordance with the invention, a relative motion of the dispersed solid particles with respect to the carrier gas is normally generated by external forces. According to the principal active forces, for example, the following separation principles are distinguished:

impingement, impactive and centrifugal forces in deflection separators, centrifugal forces in centrifugal separators, impactive action and adhesive forces in filtering separators, and electrical forces in electrofilters.

In other words, waste air cleaning apparatus which employs a mechanical separating operation and is suitable in accordance with the invention includes, for example, chamber, impingement and centrifugal separators which utilize gravitational forces. However, acoustic separators can also be employed for the process according to the invention. Preference is given to aerocyclones. In a simple manner, it is, however, also possible in accordance with the invention to filter as the mechanical separating operation.

Useful filter layers include, for example, filter fabric, porous filter compositions or paper web. Electrostatic separators are also employable in accordance with the invention. It will be appreciated that it is also possible in accordance with the invention to employ different mechanical separating operations connected in series.

The mechanical separating operation preferred in accordance with the invention is filtering, given that it is thus possible in a comparatively simple manner to capture particles with a longitudinal dimension of 0.001 μm and less (the solids content of the filtered waste air in the process according to the invention is generally at values of ≤0.1 mg/m$^3$).

In the case of appropriate dimensions and selection of the filter material, it is possible in a relatively inexpensive manner to achieve degrees of separation of more than 99.9%.

In filtering, the separating action is based essentially on impactive action (impact of the ultrafine particles on the filter element) and diffusion, though other factors such as gravity and electrostatic forces also have an influence. Even though filtration is not a pure sieving operation (the particles separated by filtration are frequently much smaller than the pores of the filter medium), narrow-mesh filters have a higher efficacy than wide-mesh filters in the inventive filtration. Appropriately in application terms, fabric filters among others can be used for the process according to the invention. In principle, for the inventive filtration, filter fabrics made of natural or synthetic fibers are suitable. In other words, they include both filter fabrics made of PVC, polyamides (PERLON®, NYLON®), wool, polyacrylonitrile (REDON®, DRALON®), polyester and polytetrafluoroethylene (TEFLON®), and made of siliconized glass fabric.

Generally, suitable filters for the process according to the invention are those as also used in air conditioning and ventilation systems. Favorable fire performance of the filter material in the sense of DIN 53438 is preferred. Incidentally, the procedure may be as described in DE-A 103 60 396 using the example of an air filtration. In-house studies have shown that the content in the relevant waste air of solid ultrafine particles (solid particles FP) prior to the performance of an inventive mechanical separating operation is generally ≥20 mg/m$^3$.

On attainment of an adjustable rise in pressure drop in the filtration, the separated solids particles FP can, for example, be separated from the filter fabric by tapping and recycled as described into process stage B) (preferably batchwise). A possible embodiment of fabric or nonwoven filters for the inventive filtration is that of bag filters.

The process according to the invention is suitable especially for producing those geometric shaped catalyst bodies K which comprise, as the active material, a multielement oxide in which the element Mo is that element E other than oxygen which is present the most frequently in the multielement oxide in numerical terms (calculated on a molar basis) of all elements E of the multielement oxide other than oxygen.

More particularly, the process according to the invention is suitable for producing those geometric shaped catalyst bodies K which comprise, as an active material, a multielement oxide which, based on the molar total amount of its elements E other than molecular oxygen, comprises the element Mo to an extent of least 30 mol %, preferably to an extent of at least 40 mol % and more preferably to an extent of at least 45 mol %.

In general, geometric shaped catalyst bodies K produced in accordance with the invention will comprise, as an active material, a multielement oxide which, based on the molar total amount of its elements E other than molecular oxygen, comprises the element Mo to an extent of not more than 90 mol % ($\leq 90$ mol %) or to an extent of not more than 80 mol % ($\leq 80$ mol %).

Finely divided mixtures M suitable for the process according to the invention can be prepared, for example, as described in the prior art (cf., for example, German Application 10 2008 042 064.6, German Application 10 2008 042 061.1, German Application 10 2008 042 060.3, German Application 10 2008 040 093.9, German Application 10 2008 040 094.7, German Application WO 2005/030393, EP-A 467 144, EP-A 1 060 792, DE-A 198 55 913, WO 01/68245, EP-A 1 060 792, Research Disclosure RD 2005-497012, DE-A 10 2005 035 978, DE-A 10 2005 037 678, WO 03/78059, WO 03/078310, DE-A 199 22 113, WO 02/24620, WO 02/062737, DE-A 10 2007 028 332, DE-A 10 2007 025 869, DE-A 10 2007 017 080 and US-A 2005/0131253).

The finely divided mixtures M are obtainable in a very simple manner by, with sources Q of the elements E other than oxygen in the desired catalytically active multielement oxide (i.e. with starting compounds which each comprise at least one element E in chemically bound form) and shaping assistants for additional use if required (e.g. porosity agents, anticaking agents, lubricants and reinforcing agents), generating a finely divided mixture M in the manner required in accordance with the invention, whose composition is aligned to the desired stoichiometry of the catalytically active multielement oxide.

The sources Q of the elements E used (the starting compounds which comprise at least one element E) may be element oxides (e.g. metal oxides) (which are generally present in the solid state of matter under standard conditions) and/or those chemical compounds comprising at least one element E (e.g. at least one metal E) which are convertible by heating (thermal treatment at elevated temperature) to oxides (which are generally in the solid state of matter under standard conditions) (at least by thermal treatment in the presence of gaseous molecular oxygen and/or of components which release gaseous oxygen). In principle, the oxygen source may, for example, be part of the finely divided mixture M in the form of a peroxide. Quite generally, one starting compound may be the source of more than one element E. Aggregate H, fines F and solid particles FP are not normally used as sources Q.

The finely divided mixture M may also comprise added compounds such as $NH_4OH$, $(NH_4)_2CO_3$, $NH_4NO_3$, urea, $NH_4CHO_2$, $NH_4CH_3CO_2$, ammonium oxalate and/or organic components, for example stearic acid, starch (e.g. potato starch, corn starch), ground nutshells, fine polymer granule (for example polyethylene, polypropylene), cellulose, graphite, malonic acid, salts of stearic acid, salts of malonic acid, inter alia, which function as pore formers in the course of the thermal treatments of the shaped bodies $V^+$ by decomposing to compounds which release in gaseous form and/or disintegrating (for example to give ammonia, steam, $CO_2$, CO and/or nitrogen oxides).

In the course of the thermal treatment of shaped bodies $V^+$, pore-forming gaseous compounds are normally also formed (released) when the sources Q with which the finely divided mixture M is obtained are partly of organic nature (for example in the case of acetates, oxalates and/or citrates) or comprise hydroxide ions, carbonate ions, hydrogencarbonate ions, ammonium ions, hydrogenphosphate ions and/or nitrate ions, which generally at least partly decompose in the course of the inventive thermal treatment of the shaped bodies $V^+$.

In general, the weight loss which is associated with the thermal treatment of the shaped bodies V (owing to the aforementioned outgassing), based on the starting weight thereof, is 0.5 to 40% by weight, frequently 0.8 to 35% by weight, or 2 to 30% by weight.

In addition, the finely divided mixture M may comprise, as further added shaping assistants, lubricants whose presence is advantageous both in process stage B) and in process stage D), by virtue of them having friction-reducing action. The lubricants of this kind used may, for example, be graphite, carbon black, polyethylene glycol, stearic acid, salts of stearic acid, malonic acid, salts of malonic acid, starch, polyacrylic acid, mineral oil, vegetable oil, water, boron nitride, boron trifluoride, glycerol, fine Teflon powder and/or cellulose ether. Preferably in accordance with the invention, exclusively fine graphite is used as the lubricant. Graphites added with preference are Asbury 3160 and Asbury 4012 from Asbury Graphite Mills, Inc., New Jersey 08802, USA, and TIMREX® T44 from Timcal Ltd., 6743 Bodio, Switzerland.

The group of the shaping assistants which may be present in the finely divided mixture M in finely divided form also include the anticaking agents.

These are finely divided materials which can be used additionally in order to very substantially suppress, for example, reagglomeration ("caking") of particles within the finely divided mixture M in the course of mixing, since such a reagglomeration might influence the effective particle diameter. A group of finely divided anticaking agents preferred in accordance with the invention is that of finely divided hydrophobized silicas, especially finely divided hydrophobized synthetic silicas (silicon dioxides).

Synthetic silicas can firstly be obtained directly by pyrogenic means from sand, and secondly by precipitation reactions from waterglass. Especially synthetic silicas are hydrophilic owing to their surface OH groups, i.e. they are wetted by water. For example, by reaction of these surface OH groups with chlorosilanes, it is possible to produce hydrophobized products both from the fumed (pyrogenic) silicas and from the precipitated silicas. For example, the hydrophobization can be effected by reaction with dimethyldichlorosilane in the presence of steam at approx. 400° C. in a fluidized bed reactor (is preferably employed in the case of fumed silicas).

Especially in the case of precipitated silicas, the chlorosilane is added to the precipitation suspension at a temperature of 50 to 90° C. with thorough stirring. This is followed by filtration, washing to neutrality with water, drying of the filtercake and heat treatment at 300 to 400° C. H. Brunner, D. Schutte, Chem. Ing. Techn. 89, 437 (1965), and DT 24 35 860 and DT 11 17 245, describe the preparation of hydrophobized finely divided silicas in detail. Commercial hydrophobized precipitated silica products are, for example, the SIPERNAT® brand.

Preferably in accordance with the invention, the finely divided SIPERNAT® D17 anticaking agent from Degussa or from EVONIK Industries are used additionally. SIPERNAT® D17 comprises, based on its weight, about 2% by weight of chemically bound carbon and is not wetted by water. Its tapped density (to ISO 787-11) is 150 g/l. Its $d_{50}$ value is 10 μm (laser diffraction to ISO 13320-1) and the specific surface area (nitrogen adsorption to ISO 5794-1, Annex D) is 100 $m^2/g$.

The addition of anticaking agents to the finely divided mixture M also reduces the energy input required for homogeneous mixing thereof. In order to promote the internal cohesion of the press agglomerates obtained in the course of the process according to the invention, it is also possible to add to the finely divided mixture M, as reinforcing agents, finely divided microfibers of, for example, glass, asbestos, silicon carbide and/or potassium titanate.

The shaping assistants added either escape in gaseous form in the course of thermal treatment of the shaped bodies V, or remain as essentially inert diluents in the resulting shaped catalyst bodies K.

For the determination of the particle diameter $d_{50}^M$ (or $d_X^M$ in general), the finely divided mixture M is conducted by means of a dispersing channel into the Sympatec RODOS dry disperser (Sympatec GmbH, System-Partikel-Technik, Am Pulverhaus 1, D-38678 Clausthal-Zellerfeld), and dry-dispersed there with compressed air and blown into the test cell in a free jet. The volume-based particle diameter distribution is then determined therein to ISO 13320 with the Malvern Mastersizer S laser diffraction spectrometer (Malvern Instruments, Worcestershire WR14 1AT, United Kingdom). The particle diameters $d_X^M$ reported as the measurement result are defined such that X % of the total particle volume of the finely divided mixture M consists of particles with this or a smaller diameter.

This means that (100-X) % of the aforementioned total particle volume consists of particles with a diameter of >$d_X^M$. Unless explicitly stated otherwise in this document, particle diameter determinations on the finely divided mixture M and $d_X^M$ inferred therefrom (and on other finely divided mixtures) are based on the above-described determination method and on a dispersion pressure (which determines the extent of the dispersion of the powder during the measurement) of 2 bar absolute employed in the determination.

In this document, the term "multielement oxide" does not mean a simple mixture of different element oxides, but rather a complex polyoxy compound which, as well as oxygen, comprises at least the elements E relevant in accordance with the invention.

When, as in this document, semimetals such as phosphorus, antimony, arsenic and silicon are counted among the metals, many multielement oxide active materials of the geometric shaped catalyst bodies K obtainable in accordance with the invention are multimetal oxides, and the elements E are metals. In principle, the multielement oxide active materials of the geometric shaped catalyst bodies K may, however, also comprise nonmetals, for example the element sulfur, as elements E. However, these cases are usually the exception.

In principle, the finely divided mixture M can be obtained exclusively by simply mixing finely divided dry starting compounds.

Preferably in accordance with the invention, in the course of generation of the finely divided mixture M, at least two different sources Q of different elements E in aqueous medium are mixed with one another, preferably with the proviso that at least one of the at least two sources Q passes through the state of an aqueous solution. Subsequently, the resulting aqueous mixture can be dried (for example by spray drying, or by freeze drying, or by simple evaporative concentration), the resulting dry mass can be comminuted if required, and the finely divided dry mass can subsequently be mixed with the remaining finely divided constituents of the finely divided mixture M.

More preferably in accordance with the invention, in the course of generation of the finely divided mixture M, at least three different sources Q of different elements E are mixed with one another in an aqueous medium, preferably with the proviso that at least one (more preferably at least two) of the at least three sources Q passes through the state of an aqueous solution. Subsequently, the resulting aqueous mixture can be dried (for example by spray drying, or by freeze drying, or by simple evaporative concentration), the resulting dry mass can be comminuted if required, and the finely divided dry mass can subsequently be mixed with the remaining constituents of the finely divided mixture M.

It will be appreciated that it is also possible in the process according to the invention to mix all sources Q of the elements E used to obtain the finely divided mixture M with one another in aqueous medium. This again is preferably with the proviso that at least one (preferably at least two) of the sources Q used overall passes through the state of an aqueous solution. Subsequently, the resulting aqueous mixture can be dried (for example by spray drying, or by freeze drying, or by simple evaporative concentration), the resulting dry mass can be comminuted if required, and the finely divided dry mass can subsequently, if appropriate, be mixed with finely divided shaping assistants for additional use to give the finely divided mixture M. It will be appreciated that, in all aforementioned process variants, the finely divided shaping assistants may already have been incorporated at least partly or else in their entirety into the aqueous mixture of the sources Q (prior to the drying of this aqueous mixture). This is especially true of porosity agents soluble in aqueous medium. Anticaking agents, lubricants and reinforcing agents, in contrast, are preferably incorporated dry into the remaining constituents of the finely divided mixture M.

Based on the total amount of the finely divided mixture M, the total amount of the shaping assistants present therein will generally not be more than 30% by weight, usually not more than 20% by weight and in many cases not more than 10% by weight. Typically, the aforementioned proportion by weight will, however, be ≥0.5% by weight.

A supplementary addition of finely divided shaping assistant can be undertaken in the process according to the invention to the powder P prior to the press agglomeration thereof to give the geometric shaped bodies V. This addition can be effected prior to and/or after the conveying of the powder P from process stage C) into process stage D). In other words, the powder P can be conveyed from process stage C) into process stage D) prior to and/or after the addition of finely divided shaping assistant.

When the addition is effected prior to the conveying of the powder from process stage C) into process stage D), this conveying of the powder P into process stage D) is normally effected in a mixture with the added finely divided shaping assistant.

Overall, the total amount of shaping assistants present in the geometric shaped bodies V in the process according to the invention should also not exceed 30% by weight based on the weight of the shaped bodies V. This proportion by weight is usually ≤20% by weight and in many cases ≤10% by weight. In general, this proportion by weight is, however, ≥1% by weight.

Preferably in accordance with the invention, the particle diameter $d_{50}^M$ is ≥1 and ≤125 μm, more preferably ≥1 and ≤100 μm, advantageously ≥5 and ≤75 μm and most preferably ≥10 and ≤50 μm. In the latter two cases, it is also advantageous when at most 10% by weight of the total weight of the particles present in the finely divided mixture M have a particle diameter $d^M$ of ≥125 μm or ≥100 μm.

The adjustment of the particle size can be undertaken on the route of preparation of the finely divided mixture M, for example, by grinding of the starting materials used and/or by spray drying of appropriate aqueous mixtures (e.g. solutions).

The thermal treatment of geometric shaped bodies V produced in accordance with the invention can be effected under reduced pressure, under inert atmosphere (e.g. $N_2$, noble gases, steam, $CO_2$ etc.), under a reducing atmosphere (e.g. $H_2$ or $NH_3$) or under an oxidizing atmosphere.

In general, oxidizing atmospheres will comprise molecular oxygen. Typical oxidizing atmospheres are mixtures of inert gas ($N_2$, noble gases, steam, $CO_2$ etc.) and molecular oxygen. Typically, the content of molecular oxygen will be at least 0.1% by volume, frequently at least 0.2% by volume, in many cases at least 0.5% by volume, often at least 1% by volume, or at least 10% by volume, or at least 20% by volume.

It will be appreciated that the content of molecular oxygen in such mixtures may also be 30% by volume, or 40% by volume, or 50% by volume or more. It will be appreciated that another useful oxidizing atmosphere for such a thermal treatment is pure molecular oxygen. Frequently, an oxidizing thermal treatment will be effected under air.

Generally, the thermal treatment can be effected under a standing or under a flowing gas atmosphere (for example in an air stream).

The term "atmosphere" (or "gas atmosphere") in which the thermal treatment is effected should be understood in this document such that it does not comprise gases which evolve owing to decomposition processes and/or chemical reaction processes from the geometric shaped bodies V produced in accordance with the invention in the course of the thermal treatment. It will be appreciated that the gas atmosphere in which the thermal treatment is effected may, however, also consist exclusively or partly of these gases. It is also possible for both the treatment temperature and the treatment atmosphere to be configured so as to be constant with time or variable with time over the duration of the thermal treatment.

In general, the thermal treatment is effected at temperatures of 150 to 650° C., in many cases 200 to 600° C., often 250 to 550° C. and in many cases 300 to 500° C.

When the powder P or P* press agglomerated to geometric shaped bodies V comprises ammonium, formate, acetate and/or nitrate ions, it has been found to be advantageous for the performance of the geometric shaped catalyst bodies K (especially the selectivity of target product formation) when the contents $G^W$ in the geometric shaped bodies V (or of the powders P, P*) of water, based on the total weight of the total amount of ammonium, formate, acetate and nitrate ions present in the geometric shaped bodies V, is ≤60% by weight, advantageously ≤50% by weight, or ≤40% by weight and even better ≤35% by weight. In general, the content $G^W$ will be ≥15% by weight and in some cases ≥20% by weight.

This connection is presumably attributable to the fact that salts of the aforementioned ions are capable of binding water to a certain degree without any dissolution phenomena.

When the water content exceeds this binding capacity, the water may bring about dissolution and/or chromatography effects (for example especially in the initial stages of the thermal treatment of the shaped bodies V) (in particular of the elements Co, Ni, Fe, Cu and the alkali metals), which are accompanied by local enrichments and depletions of elements E in the overall structure, which impair the catalytic activity.

This is especially true when the multielement oxide active material comprises Co.

Owing to the inventive recyclings into process stage B), which increase the residence time of salts of the relevant ions in the production process, it is appropriate in application terms for the achievement of the aforementioned water contents to employ at least one of the following additional measures:

in the removal of solid particles FP dispersed in the waste air from the different process stages B) to G) by, for example, filtering of the waste air, large amounts of waste air flow through the filtercake; advantageously in application terms, process stages B) to G) are therefore performed in climate-controlled rooms whose ambient air is continuously demoistened by means of a climate control system;

finely divided materials are conveyed from process stage C) into process stage D) pneumatically by means of elevated pressure;

when the recycling into process stage B) is effected batchwise in an advantageous manner in application terms, the fines F, the aggregate H and the solid particles FP removed are advantageously collected and stored in closed vessels;

spray dryings of aqueous mixture in the course of preparation of the finely divided mixture are appropriately performed by means of dried hot gas streams and at elevated starting temperatures;

finely divided mixture M, mixture M*, agglomerates A, powders P and P* and shaped bodies V are stored intermediately in closed vessels;

keep the proportion of fines F, aggregate H and solid particles FP for recycling in the finely divided mixture M* low.

The contents $G^W$ in the geometric shaped bodies V (and in the powders P, P*) of water, which should be complied with advantageously in accordance with the invention, are of relevance not least when the geometric shaped bodies V (or the powders P, P*) are acidic, since an acidic environment increases the tendency to dissolve. The property "acidic" shall be present when 10 mg of a shaped body V (of the powder P or P*) is stirred in 10 ml of multidistilled water (pH=7 at 25° C., 1 atm) at 25° C. and 1 atm for min, and the pH of the aqueous medium thereafter is at most 6 (or 5 or 4) (at 25° C., 1 atm) (pH≤6). This is true in particular when the geometric shaped body V (or the powder P or P*) additionally comprises nitrate ions.

The absolute content of water in shaped bodies V or powder P or P* can be determined, for example, by selectively evaporating the water present by means of incident microwaves and determining the associated weight loss.

Quite generally, in the course of preparation of a finely divided mixture M, the sources Q used for this preparation are preferably mixed in wet form. Typically, the starting compounds comprising the elements E are mixed with one another in the form of an aqueous solution and/or suspension. Particularly intimate mixtures are obtained when the starting materials are exclusively sources Q of the elemental constituents in dissolved form, water being the preferred solvent. Subsequently, the resulting solution or suspension is dried, the drying process preferably being effected by spray drying with exit temperatures of 100 to 150° C. (in some cases, the drying can, however, also be effected by filtration and subsequent drying of the filtercake). The particle diameter $d_{50}$ of the resulting spray powder is typically 10 to 50 µm. After addition (or else without such an addition) of the desired shaping assistants to the particular dry mass in pulverulent form, a finely divided mixture M results. However, the finely divided shaping assistants can also be added (partly or fully) beforehand to the spray mixture.

An only partial removal of the solvent or suspension medium may be appropriate in application terms when its additional use as a shaping assistant is intended.

If water was the basis of the liquid medium, the resulting spray powder will normally comprise not more than 20% of its weight, preferably not more than 15% of its weight and more preferably not more than 10% of its weight of water. These percentages generally also apply in the case of the use of other liquid dissolving or suspending assistants.

Typically, the finely divided mixture M and the finely divided mixture M* in the process according to the invention are dry to the touch. As mentioned above, it may, however, also comprise substances which are liquid under standard conditions (25° C., 1 atm). It may also be entirely free of such substances.

When the geometric shaped catalyst body K produced in accordance with the invention, as an active material, comprises a multielement oxide which comprises at least one alkali metal, the at least one alkali metal is advantageously K, Na, Cs and/or Rb, and particularly advantageously K, Na and/or Cs, or K and/or Na.

The longest dimension L of the agglomerates A obtained in process stage B) depends not least on the press agglomeration process employed. The longest dimension L is understood to mean the longest direct line connecting two points on the surface of the agglomerate A. In general, in the process according to the invention, it will be $\geq 0.5$ cm, in many cases $\geq 1$ cm, or $\geq 3$ cm, frequently $\geq 5$ cm or $\geq 10$ cm. In most cases, the longest dimension L is, however, $\geq 1$ m.

Press agglomeration is understood in this document to mean the agglomeration of pulverulent solids through the action of external pressing forces. In process stage B), this can be done, for example, by compacting a defined amount of the finely divided mixture M* in a die with a punch (tableting). Advantageously in accordance with the invention, the press agglomeration in process stage B) is effected by roll pressing. In this method, the finely divided mixture M* is drawn in between two rotating rollers and compacted in the roller gap. The finely divided mixture M* can be supplied to the rollers only with the aid of gravity by means of a filling funnel or by means of a supply unit. Preferably in accordance with the invention, the supply unit used is a filling funnel with integrated stirring device and screw conveying. The mass flow in the screw conveyor has to be matched to the capacity of the downstream roller press. The conveying screw is configured such that the material to be agglomerated in the roller press is already preliminarily deaerated and preliminarily compacted on the route of the conveying thereof in the roller gap.

In addition, the screw for conveying the finely divided mixture M* preferably extends into the interstitial region between the mutually opposite rollers. The roller surface may be smooth or have open or closed profiles. Preference is given in accordance with the invention to using smooth rollers and particular preference to using rollers with open profiles. They generate an agglomerate in ribbon form, which breaks into pieces, also known as "slugs", along the ribbon length when detached from the roller.

The screw preferably has an essentially vertical axis of rotation.

It may have a decreasing slope along the conveying direction thereof and/or a decreasing diameter along the direction of conveying. The conveying chamber in which the screw is arranged may have a smooth inner wall. However, it may also have a groove running in the form of a helix about the direction of conveying of the screw, in order to promote the advancing action of the screw.

The rollers or at least the roller surfaces may be formed from metal (stainless steel), thermoplastic or thermoset, and/ or from an elastomer.

In principle, roller presses are available in two different designs: with a fixed gap width or with a variable gap width. In the latter case, one of the two rollers, the so-called loose roller, is mounted so as to be shiftable (it is used with preference in accordance with the invention). With the aid of a pressing device, a stable operating state of the machine is ensured. In a simple configuration, the pressing system consists of spring assemblies. Preference is given in accordance with the invention to a hydraulic pressing apparatus which enables exact matching of the pressure to the finely divided mixture M* for agglomeration and to varying reactant mass flows. The configuration of the roller surface determines the intake behavior of the mixture M*; the adjustable speed of the rollers fixes the residence time of the material in the compacting space, an infinitely adjustable hydraulic unit generates the necessary pressure and transmits it to the rollers, the hydraulic system keeps the established roller pressure constant and thus ensures a homogeneous slug, and strippers keep the rollers clean.

Particularly suitable apparatus for process stage C) of the process according to the invention is the 200/100 two-roller compactor from Hoskawa Bepex GmbH, D-74211 Leingarten, with concave, fluted smooth rollers and variable gap width.

Typically, the slugs produced in process stage B) in the process according to the invention have a thickness of a few mm (e.g. 3 mm) and a width of a few cm (e.g. cm). Otherwise, the procedure may, for example, be as recommended in WO 2008/014839 or in "Modellierung der Pressagglomeration feinkörniger, kohäsiver und kompressibler Schüttgüter" [Modeling of the Press Agglomeration of Fine Particulate, Cohesive and Compressible Bulk Materials], Thesis, Lilla Grossmann, Otto-von-Gueicke University of Magdeburg, Jun. 13, 2006. It will be appreciated that all other methods of press agglomeration known in the prior art are also useful in process stage B). The maximum (highest) pressures P1 applied in process stage B) are guided by the individual properties of the particular finely divided mixture M*.

In general, it is selected such that the material is compacted 1.5- to 3-fold (ratio of the mass densities). Typical maximum pressures P1 are 0.1 to 5 and frequently 2 to 4 kN/cm².

It is essential to the invention that the maximum (highest) pressure P2 satisfies the relationship $P2 \geq 2 \cdot P1$. However, the process according to the invention is also employable when $P2 \geq 3 \cdot P1$, or $P2 \geq 4 \cdot P1$, or $P2 \geq 6 \cdot Pb1$, or $P2 \geq 8 \cdot P1$. In general, P2, however, will not be more than $20 \cdot P1$, frequently not more than $15 \cdot P1$.

In the process according to the invention, the agglomerates A obtained in process stage B) are subsequently comminuted in process stage C) to the desired particle size (in principle, it is possible to use all known comminution apparatus for this purpose). Advantageously, the comminution is effected with a low level of fines.

When agglomeration has been effected in process stage B) by means of roller presses, the slugs obtained are, appropriately in application terms, first crushed. Advantageously for this purpose, in the process according to the invention, a GBM-406 pin crusher machine from Frewitt-Maschinenfabrik AG in CH-1700 Fribourg is used.

It consists internally of a counterclockwise-rotating roller (equipped with pins), the so-called pinned roller. This is surrounded on both sides by perforated or slotted impingement plates. The particle size after the crushing operation is established by the sizes of the holes or slots (orifices in general) in the impingement plate and by the distances of the impingement plates from the pinned roller.

After the aforementioned coarse comminution, in which comparatively sharp-edged fragments are obtained, they are, appropriately in application terms, fed to a sieve mill, preferably a rotor sieve mill. Preferably in accordance with the invention, an MGR-803 sieve mill from Frewitt-Maschinenfabrik AG in CH-1700 Fribourg is used for this purpose.

This agitated sieving machine consists of a rotor and a perforated sieve (the basic structure of such an agitated sieving machine is shown by way of example by FIG. 3 of WO 2008/014839). Rotating rotor arms are used to force the pre-crushed slugs through the orifice of a conically curved sieve, which comminutes them mechanically to the particle size defined by the sieve orifices. In terms of application, the sieve consists of rectangular wire and has square meshes as sieve holes (sieve orifices).

The drive bearing of the rotor causes heating of the parts in contact with the product and thus a temperature rise of the powder material. This should generally not exceed 70° C.

A by-product obtained in the comminution described is undesired fines.

These fines F (which do not normally have a degree of comminution less than the degree of comminution of the finely divided mixture M) can, for example, be removed as undersize by means of a vibrating sieve, in which case the mesh size of the vibrating sieve fixes the oversize/undersize diameter limit. For example, vibrating sieves from Allgaier in D-73062 Uhingen are suitable for this separation step, for example those of the ATS 600 type.

The fines F thus removed (it may be up to 50% by weight or more of the total amount of particles; preferably in accordance with the invention, it is ≤40% by weight, or ≤30% by weight, of the total amount) are recycled in the process according to the invention batchwise or continuously to the incorporation into finely divided mixture M* in process stage B), while the oversize obtained in the sieve removal is conveyed into process stage D). Prior to or after this conveying, finely divided shaping assistants can be added to the powder P (for example graphite as a lubricant for the press agglomeration in the downstream process stage D)). Advantageously in accordance with the invention, the conveying of the powder P from process stage C) alone or in a mixture with finely divided shaping assistant (as powder P*) is performed pneumatically. This is understood to mean the transport of the powder with gas (for example with air (preferably dried air; the air drying can be performed, for example, by means of BASF SORBEAD®, the air being conducted through a bed thereof) or with inert gas, for example $N_2$ and/or $CO_2$) by means of elevated pressure ("pressure pneumatics") or by means of reduced pressure ("suction pneumatics").

In terms of principle, the conveying takes place through tubes or hoses.

In principle, the conveying can be effected as aerial delivery (gas velocity ≥20 m/s, based on the empty tube; conveyed material is blown or sucked through the conveying line while suspended; ratio of conveyed material to conveying gas (the loading) is <15 kg/kg, the contact with the tube wall, particularly in changes of direction, is so intensive that wear and particle fracture occur), strand conveying (gas velocity 15 to 20 m/s, some of the conveyed material slides as strands over the base of the tube and is driven onward by the particles flying above them, loading is in the range of 20 to 40 kg/kg), plug conveying (the conveying line is filled with conveyed material to such an extent that the conveyed material is shifted through the line as one or more material plugs; loading >40 kg/kg to 200 kg/kg, gas velocity 3 to 10 m/s), or else as flow conveying (gas-solid mixture behaves like a continuum, loadings up to 300 kg/kg or 400 kg/kg, gas velocity 7 to 15 m/s). Preferably in accordance with the invention, aerial conveying is employed with very substantial avoidance of changes of direction. The preferred conveying tube material is stainless steel.

In principle, the desired geometry of the resulting shaped bodies V in the process according to the invention is not subject to any restriction. In other words, the geometric shaped bodies V may have either a regular or irregular shape, preference being given in accordance with the invention to regularly shaped bodies V.

For example, the shaped body V in the process according to the invention may have spherical geometry. The sphere diameter may, for example, be 2 to 10 mm, or 4 to 8 mm.

The geometry of the shaped body V (of the shaped catalyst precursor body) may, however, also be solid cylindrical or hollow cylindrical (annular). In both cases, external diameter (A) and height (H) may, for example, be 2 to 10 mm, or 2 or 3 to 8 mm. In the case of hollow cylinders (rings), a wall thickness of 1 to 3 mm is generally appropriate. However, it will be appreciated that useful catalyst precursor geometries are also all of those which are disclosed and recommended in WO 02/062737.

The shaping pressures employed in process stage D) are guided in the process according to the invention by the particular specific properties of the powder P or P* to be shaped. In general, the maximum shaping pressures P2 employed in process stage D) are 500 to 50 000 N/cm², preferably 2000 to 35 000 N/cm², and more preferably 6000 to 25 000 N/cm².

Preferably in accordance with the invention, the press agglomeration in process stage D) is effected by tableting. The tableting can be performed, for example, as described in documents EP-A 184790, US 2005/0263926, JP-A 10/29097, and WO 2005/030393. Preferably in accordance with the invention, the tableting in the process according to the invention is performed as described in documents DE-A 10 2008 040 093 and DE-A 10 2008 040 094, especially with regard to the side crushing strength SC of the resulting annular or ringlike shaped body V.

The experimental determination of the side crushing strength is performed as described in documents WO 2005/030393 and WO 2007/017431.

Of course, ringlike shaped bodies V as recommended by DE-A 10 2008 040 093 are very particularly preferred in accordance with the invention. The end face of annular or ringlike shaped bodies V in the process according to the invention may be either curved or uncurved (cf. especially DE-A 10 2007 004 961, EP-A 184790, and DE-A 10 2008 040 093). In determining the height of such geometric shaped bodies V, such curvature is not taken into account.

In principle, the thermal treatment of shaped bodies $V^+$ to obtain the geometric shaped catalyst bodies K can be performed in a wide variety of different oven types, for example heatable forced air chambers (forced air ovens), staged ovens, rotary tube ovens, belt calciners or shaft ovens. Advantageously in accordance with the invention, the thermal treatment of the shaped bodies $V^+$ is effected in a belt calcining apparatus, as recommended by DE-A 100 46 957, and WO 02/24620.

Hotspot formation within the calcination material is very substantially avoided by virtue of increased volume flows of calcination atmosphere being conveyed through the calcination material on a gas-permeable conveyor belt which bears the calcination material with the aid of ventilators. The belt calcination is generally completed by a cooling zone. In the cooling zone, cooling ribs through which a cooling medium flows are present above and below the gas-permeable conveyor belt. With the aid of ventilators, the completed gas atmosphere of the cooling zone is circulated and it is cooled on contact with the cooling ribs.

The comminution of non-intact shaped bodies V to the particle size required for the process according to the invention is, appropriately in application terms, performed with the aid of a hammer mill (also known as "impact mill") (in principle, it is, however, also possible to use other mills). In these mills, the millbase is comminuted by the effect of kinetic impact. In a metal casing, a rotor rotates, on whose outer periphery a number of moveable steel hammers are mounted, which are brought to peripheral speeds of up to 120 m/s. On entry into the circle of impact of the rotor, the millbase meets the rotating hammers.

The impact of the hammer achieves the greatest comminution effect. The hammers also throw the pieces against the mill wall, where they are broken further by the impact. A further comminution proceeds in the lower region between rotor and mill wall. The millbase remains in the comminution zone until it is sufficiently small that it fits through a perforated (orifice) sieve at the outer periphery of the machine. The sieve fulfills the function of limiting the upper particle size.

Normally, the hammer mill does not achieve a degree of comminution below that of the finely divided mixture M. In other words, in the hammer mill, essentially only cohesive contact points of the primary particles are broken up into their agglomerates formed by the press agglomeration.

Preferably in accordance with the invention, the above comminution is performed with a hammer mill from Hosokawa Alpine AG in D-86199 Augsburg.

In the case that a sieve mill is used for the crushing operation in process stage B), the sieve of the sieve mill can break from time to time owing to its high mechanical stress. By means of a protective sieve mounted above the vibrating sieve for the fines F, coarse fragments emerging from the mill are intercepted in this case. They can likewise be supplied to process stage G) and comminuted there together with the shaped bodies $V^-$ to give the aggregate H) for recycling into process stage B) (for example in a hammer mill as described).

The particle diameters $d^P$ in the process according to the invention are frequently also ≤1.5 mm and in many cases ≤1 mm. Furthermore, the particle diameters $d^P$ in at least 90% by weight (preferably in at least 95% by weight or in 100% by weight), based on the total weight of the powder P, of the particles of the powder P are ≥200 µm, or ≥300 µm, or even ≥400 µm.

For the process according to the invention, it is additionally advantageous when the particle diameters $d^H$ are ≤150 µm, preferably ≤130 µm, more preferably ≤110 µm and most preferably ≤100 µm.

It should also be emphasized at this point that, in the case of batchwise recycling of finely divided material in the process according to the invention, this finely divided material is first collected under level control in collecting vessels provided for this purpose.

On attainment of the fixed fill level, the particular collecting vessel is then emptied in a recycling manner.

Geometric shaped catalyst bodies K produced in accordance with the invention are suitable in particular as catalysts for heterogeneously catalyzed partial oxidations of organic compounds. In particular, these are the partial oxidations of propene to acrolein, of isobutene or tert-butanol or the methyl ether thereof to methacrolein or to methacrylonitrile, of propene to acrylonitrile, of acrolein to acrylic acid and of methacrolein to methacrylic acid (partial oxidations in the presence of ammonia, so-called ammoxidations, shall likewise be included under the term "partial oxidations" in this document).

All statements made so far in this document are valid in particular for the production of the geometric shaped catalyst bodies K described in the documents of German Applications 102008040094.7, 102008040093.9, 102008042060.3, 102008042061.1, and 102008042064.6.

More particularly, they are valid when the catalytically active multielement oxide of the geometric (e.g. annular or ringlike) multielement oxide unsupported catalyst (shaped catalyst body K) has a stoichiometry of general formula I $$Mo_{12}Bi_aFe_bX^1_cX^2_dX^3_eX^4_fO_n \qquad (I)$$

where
$X^1$=nickel and/or cobalt,
$X^2$=thallium, samarium, an alkali metal and/or an alkaline earth metal,
$X^3$=zinc, phosphorus, arsenic, boron, antimony, tin, cerium, lead, vanadium, chromium, niobium and/or tungsten,
$X^4$=silicon, aluminum, titanium and/or zirconium,
a=0.2 to 5,
b=0.01 to 5,
c=0 to 10,
d=0 to 2,
e=0 to 8,
f=0 to 10, and
n=a number which is determined by the valency and frequency of the elements in I other than oxygen,
or a stoichiometry of the general formula II $$[Y^1_{a'}Y^2_{b'}O_{x'}]_p[Y^3_{c'}Y^5_{e'}Y^6_{f'}Y^7_{g'}Y^8_{h'}O_{y'}]_q \qquad (II)$$

where
$Y^1$=only bismuth or bismuth and at least one of the elements tellurium, antimony, tin and copper,
$Y^2$=molybdenum or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements vanadium, chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum or tungsten, or molybdenum and tungsten,
a'=0.01 to 8,
b'=0.1 to 30,
c'=0 to 4,
d'=0 to 20,
e'>0 to 20, f'=0 to 6,
g'=0 to 15,
h'=8 to 16,
x', y'=numbers which are determined by the valency and frequency of the elements in II other than oxygen, and
p, q=numbers whose p/q ratio is from 0.1 to 10.

Such, for example, annular or ringlike multielement oxide unsupported catalysts are suitable in particular as catalysts with increased selectivity and activity for the gas phase catalytic partial oxidation of propene to acrolein and of isobutene or tert-butanol or the methyl ether thereof to methacrolein.

The partial oxidation can be effected, for example, as described in documents WO 00/53557, WO 00/53558, German Application 10 2008 040 093.9, German Application 10 2008 040 094.7, DE-A 199 10 506, EP-A 1 106 598, WO 01/36364, DE-A 199 27 624, DE-A 199 48 248, DE-A 199 48 523, DE-A 199 48 241, EP-A 700 714, DE-A 103 13 213, DE-A 103 13 209, DE-A 10 2004 003 212 and DE-A-10 2005 013 039.

The catalyst charge may comprise only geometric shaped catalyst bodies K, or shaped catalyst bodies K diluted with inert shaped bodies. In the latter case, the catalyst charge is advantageously configured such that its volume-specific activity increases in flow direction of the reaction gas mixture.

Descriptions of the preparation of such shaped catalyst bodies K can be found, for example, in documents DE-A 10 2005 037 678, DE-A 102 007 003 778, DE-A 102 007 028 332, and in German Applications 102008040094.7, 102008040093.9, 102008042060.3, 102008042061.1 and 102008042064.6.

In the inventive process stage D), the shaping is advantageously effected such that the side crushing strength of the resulting annular or ringlike shaped catalyst body K is $\geq 10$ and $\leq 40$ N, better $\geq 10$ and $\leq 35$ N, even better $\geq 12$ N and $\leq 30$ N. The side crushing strength of the ringlike shaped catalyst bodies K is preferably $\geq 13$ N and $\leq 27$ N, or $\geq 14$ N and $\leq 25$ N. Most preferably, the side crushing strength of the ring-like shaped catalyst bodies K is $\geq 15$ N and $\leq 22$ N.

Regarding the active materials of the stoichiometry II, the stoichiometric coefficient b is preferably from 2 to 4, the stoichiometric coefficient c is preferably from 3 to 10, the stoichiometric coefficient d is preferably from 0.02 to 2, the stoichiometric coefficient e is preferably from 0 to 5 and the stoichiometric coefficient a is preferably from 0.4 to 2. The stoichiometric coefficient f is advantageously from 0.5 or 1 to 10. More preferably, the aforementioned stoichiometric coefficients are simultaneously within the preferred ranges specified.

In addition, $X^1$ is preferably cobalt, $X^2$ is preferably K, Cs and/or Sr, more preferably K, $X^3$ is preferably tungsten, zinc and/or phosphorus, and $X^4$ is preferably Si. More preferably, the variables $X^1$ to $X^4$ simultaneously have the aforementioned definitions.

More preferably, all stoichiometric coefficients a to f and all variables $X^1$ to $X^4$ simultaneously have their aforementioned advantageous definitions.

Within the stoichiometries of the general formula II, preference is given to those which correspond to the general formula III $$[Bi_{a''}Z^2_{b''}O_{x''}]_{p''}[Z^8_{12}Z^3_{c''}Z^4_{d''}Fe_{4''}Z^5_{f''}Z^6_{g''}Z^7_{h''}O_{y''}]_{q''} \quad (III)$$

where
$Z^2$=molybdenum or tungsten, or molybdenum and tungsten,
$Z^3$=nickel and/or cobalt,
$Z^4$=thallium, an alkali metal and/or an alkaline earth metal, preferably K, Cs and/or Sr,
$Z^5$=phosphorus, arsenic, boron, antimony, tin, cerium, vanadium, chromium and/or Bi,
$Z^6$=silicon, aluminum, titanium and/or zirconium, preferably Si,
$Z^7$=copper, silver and/or gold,
$Z^8$=molybdenum or tungsten, or tungsten and molybdenum,
a''=0.1 to 1,
b''=0.2 to 2,
c''=3 to 10,
d''=0.02 to 2,
e''=0.01 to 5, preferably 0.1 to 3,
f''=0 to 5,
g''=0 to 10, preferably >0 to 10, more preferably 0.2 to 10 and most preferably 0.4 to 3,
h''=0 to 1,
x'', y''=numbers which are determined by the valency and frequency of the elements in III other than oxygen, and
p'', q''=numbers whose p''/q'' ratio is from 0.1 to 5, preferably 0.5 to 2.

Additionally preferred are catalytically active multielement oxides of stoichiometry II which comprise three-dimensional regions of the chemical composition $Y^1_{a'}Y^2_{b'}O_{x'}$ which are delimited from their local environment as a consequence of their different composition than their local environment and whose largest diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous catalytically active multielement oxides of stoichiometry II are those in which $Y^1$ is only bismuth.

Within the catalytically active multielement oxides of stoichiometry III, preference is given in accordance with the invention to those in which $Z^2_{b''}$=(tungsten)$_{b''}$ and $Z^8_{12}$=(molybdenum)$_{12}$.

Additionally preferred are catalytically active multielement oxides of stoichiometry III which comprise three-dimensional regions of chemical composition $Bi_{a''}Z^2_{b''}O_{x''}$ which are delimited from their local environment as a consequence of their different composition than their local environment and whose largest diameter (longest direct line passing through the center of the region and connecting two points on the surface (interface) of the region) is from 1 nm to 100 μm, frequently from 10 nm to 500 nm or from 1 μm to 50 or 25 μm.

It is also advantageous when at least 25 mol % (preferably at least 50 mol % and more preferably at least 100 mol %) of the total $[Y^1_{a'}Y^2_{b'}O_{x'}]_p$ ($[Bi_{a''}Z^2_{b''}O_{x''}]_p$) content of the catalytically active multielement oxides of stoichiometry II (of stoichiometry III) obtainable as described in the catalytically active multielement oxides of stoichiometry II (of stoichiometry III) is in the form of three-dimensional regions of chemical composition $Y^1_{a'}Y^2_{b'}O_{x'}$($[Bi_{a''}Z^2_{b''}O_{x''}]$) which are delimited from their local environment as a consequence of their different chemical composition than their local environment and whose largest diameter is in the range from 1 nm to 100 μm.

However, the statements in this document are also valid when the catalytically active multielement oxide of the, for example, annular or ringlike multielement oxide unsupported catalyst (shaped catalyst body K) has a stoichiometry of the general formula IV $$Mo_{12}P_aV_bX^1_cX^2_dX^3_eSb_fRe_gS_hO_n \quad (IV)$$

where:
$X^1$=potassium, rubidium and/or cesium,
$X^2$=copper and/or silver, $X^3$=cerium, boron, zirconium, manganese and/or bismuth,
a=0.5 to 3,
b=0.01 to 3,
c=0.2 to 3,
d=0.01 to 2,
e=0 to 2,
f=0 to 2, preferably 0.01 to 2,
g=0 to 1,
h=0 to 0.5, preferably 0.001 to 0.5, and
n=a number which is determined by the valency and frequency of the elements in IV other than oxygen.

Preference is given to multielement oxides IV in which h is from 0.03 to 0.5.

Particularly preferred stoichiometries of the general formula IV are those of working examples B1 to B15 from EP-A 467 144, even when these illustrative multielement oxides do not comprise any K and/or any Re.

The aforementioned EP-A 467 144, and German Application 102007003778.5, and also German Applications 102008040094.7 and 102008040093.9, also describe the production of annular multielement oxide (IV) shaped unsupported catalyst bodies and the preferred use thereof as catalysts for the heterogeneously catalyzed gas phase partial oxidation of methacrolein to methacrylic acid.

In a surprising manner, the inventive recycling also has essentially no adverse effect on the long-term stability of the geometric shaped catalyst bodies in partial oxidation operation.

The present application thus comprises especially the following embodiments:

1. A process for continuously producing geometric shaped catalyst bodies K which comprise, as an active material, a multielement oxide which comprises, as elements E other than oxygen, the element Mo, at least one of the two elements Bi and V, and at least one further element from the group consisting of Co, Ni, Fe, Cu and the alkali metals, in process stages A) to G), in which
   in process stage A), with the aid of sources Q of the elements E, a finely divided mixture M is obtained with the proviso that at most 10% by weight of the total weight of the particles present in the finely divided mixture M have a particle diameter of $d^M \geq 160$ µm and the particle diameter $d_{50}^M$ of the particles of the finely divided mixture M satisfies the condition 1 µm$\leq d_{50}^M \leq$150 µm;
   in process stage B), the finely divided mixture M*, which consists either only of the finely divided mixture M or of a mixture of the finely divided mixture M and fines F which are obtained in the next process stage C) and are recycled into process stage B) continuously or batchwise from process stage C), is compacted by press agglomeration in which the maximum pressure applied is P1 to agglomerates A whose longest dimension is ≥3 mm;
   in process stage C), the agglomerates A are comminuted and the particulate material formed in the comminution is separated by sieving into a powder P whose particle diameters $d^P$ are ≤2 mm and, to an extent of at least 90% by weight, based on the weight of the powder P, ≥160 µm, as sieve oversize, and into fines F as sieve undersize, and the fines F are recycled continuously or batchwise into process stage B to obtain finely divided mixture M*;
   in process stage D), the powder P conducted into it or a mixture P* consisting of the powder P conducted into process stage D) and shaping assistants is used to obtain, by press agglomeration in which the maximum pressure applied is P2 and satisfies the relationship P2≥2·P1, geometric shaped bodies V with the proviso that when the powder P is conveyed into process stage D) and when shaping assistants are mixed into the powder P, a particle diameter $d^P$>160 µm is maintained overall in at least 40% by weight of the particles of the powder P, based on the weight thereof; and
   in process stage E), at least a portion of the shaped bodies V is treated thermally at elevated temperature to obtain the geometric shaped catalyst bodies K, wherein
   prior to process stage E), the shaped bodies V obtained in process stage D) are separated in an additional separation stage as process stage F) into non-intact shaped bodies V⁻ and into intact shaped bodies V⁺, the shaped bodies V⁺ are fed to process stage E) and
   in process stage G), non-intact shaped bodies V⁻ are comminuted to form a finely divided aggregate H whose particle diameter $d_{50}^H$ satisfies the condition 1 µm$\leq d_{50}^H \leq$150 µm and which comprises particles having a particle diameter $d^H \geq$160 µm to an extent of at most 10% by weight of its total weight, and the finely divided aggregate H is recycled continuously or batchwise to the additional incorporation into the finely divided mixture M* into process stage B) with the proviso that the content of finely divided aggregate H in the finely divided mixture M*, based on the total weight of the finely divided mixture M*, does not exceed 20% by weight.

2. The process according to embodiment 1, wherein the separation of the shaped bodies V in process stage F is undertaken by a sieve separation in which the intact shaped bodies V⁺ remain as the sieve residue and the fragments of non-intact shaped bodies V⁻ pass through the sieve.

3. The process according to embodiment 1 or 2, wherein, in at least one of the different process stages B) to G), the gas atmosphere which exists in this at least one process stage is sucked out and subjected to at least one mechanical separating operation, with which solid particles FP present in the gas atmosphere are removed, and recycled continuously or batchwise into process stage B) and incorporated into the finely divided mixture M* with the proviso that the content of such recycled solid particles FP in the mixture M*, based on the total weight of the mixture M*, does not exceed 10% by weight.

4. The process according to embodiment 3, wherein the content of recycled solid particles FP in the mixture M* does not exceed 5% by weight.

5. The process according to embodiments 3 or 4, wherein the at least one mechanical separating operation is filtration.

6. The process according to any one of embodiments 1 to 5, wherein the geometric shaped catalyst bodies K comprise, as an active material, a multielement oxide in which the element Mo is that element E other than oxygen which, of all elements E other than oxygen in the multielement oxide, is present with the greatest molar frequency in the multielement oxide.

7. The process according to any one of embodiments 1 to 6, wherein the geometric shaped catalyst bodies K comprise, as an active material, a multielement oxide which, based on the molar total amount of its elements E other than molecular oxygen, comprises the element Mo to an extent of at least mol %.

8. The process according to any one of embodiments 1 to 7, wherein the geometric shaped catalyst bodies K comprise, as an active material, a multielement oxide which comprises at least one of the alkali metals K, Na and Cs as the element E.

9. The process according to any one of embodiments 1 to 8, wherein 1 µm$\leq d_{50}^M \leq$100 µm.

10. The process according to any one of embodiments 1 to 9, wherein, in the course of obtaining the finely divided mixture M, at least three different sources Q of different elements E are mixed with one another in an aqueous medium.

11. The process according to any one of embodiments 1 to 10, wherein the powder P or P* press agglomerated to geometric shaped bodies V comprises at least one ion from the group consisting of ammonium, formate, acetate and nitrate ions, and the water content $G^W$ of the powder P or P*, based on the total weight of the total amount of ammonium, formate, acetate and nitrate ions present therein, is ≤60% by weight.

12. The process according to embodiment 11, wherein $G^W$≤50% by weight.

13. The process according to embodiment 11, wherein $G^W$≤40% by weight.

14. The process according to any one of embodiments 11 to 13, wherein the powder P or P* is acidic.

15. The process according to embodiment 14, wherein the powder P or P* comprises nitrate ions.

16. The process according to any one of embodiments 1 to 15, wherein the longest dimension L of the agglomerates obtained in process stage B) is ≥0.5 cm.

17. The process according to any one of embodiments 1 to 15, wherein the longest dimension L of the agglomerates obtained in process stage B) is ≥1 cm.

18. The process according to any one of embodiments 1 to 17, wherein the press agglomeration in process stage B) is performed with a roller press.

19. The process according to any one of embodiments 1 to 18, wherein P2≥3·P1.

20. The process according to any one of embodiments 1 to 18, wherein P2≥4·P1.

21. The process according to any one of embodiments 1 to 20, wherein the shaped body V has an annular geometry with an external diameter A and a height H of 2 to 10 mm and a wall thickness of 1 to 3 mm.

22. The process according to any one of embodiments 1 to 21, wherein the particle diameters $d^P$ are ≤1 mm.

23. The process according to any one of embodiments 1 to 22, wherein the particle diameter $d^P$ is ≥200 μm in at least 90% by weight, based on the total weight of the powder P, of the particles of the powder P.

24. The process according to any one of embodiments 1 to 23, wherein the particle diameters $d^H$ are ≤100 μm.

25. The process according to any one of embodiments 1 to 24, wherein the pressure P1 is 0.1 to 5 kN/cm².

26. The process according to any one of embodiments 1 to 25, wherein the powder P is conveyed from process stage C) into process stage D) by suction pneumatics or pressure pneumatics.

27. The process according to any of embodiments 1 to 26, wherein the content in the finely divided mixture M* of finely divided aggregate H, based on the total weight of the finely divided mixture M*, does not exceed 15% by weight.

28. The process according to any of embodiments 1 to 26, wherein the content in the finely divided mixture M* of finely divided aggregate H, based on the total weight of the finely divided mixture M*, does not exceed 10% by weight.

29. The process according to any of embodiments 1 to 28, wherein the content in the finely divided mixture M* of finely divided aggregate H, based on the total weight of the finely divided mixture M*, is at least 1% by weight.

30. The process according to any of embodiments 1 to 28, wherein the content in the finely divided mixture M* of finely divided aggregate H, based on the total weight of the finely divided mixture M*, is at least 3% by weight.

31. The process according to any of embodiments 1 to 28, wherein the content in the finely divided mixture M* of finely divided aggregate H, based on the total weight of the finely divided mixture M*, is at least 5% by weight.

32. A process for heterogeneously catalyzed partial gas phase oxidation of an organic compound, which comprises using, as the catalyst, at least one geometric shaped catalyst body K obtained by a process according to any one of embodiments 1 to 31.

33. The process according to embodiment 32, wherein the process for heterogeneously catalyzed partial gas phase oxidation is the partial oxidation of propene to acrolein, of isobutene to methacrolein, of propene to acrylonitrile, of isobutene to methacrylonitrile, of acrolein to acrylic acid or of methacrolein to methacrylic acid.

EXAMPLES AND COMPARATIVE EXAMPLES

I. Preparation of annular shaped catalyst bodies K and annular comparative shaped catalyst bodies VK, whose multielement oxide active material in each case has the following stoichiometry:

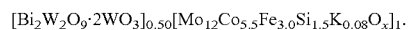

$[Bi_2W_2O_9 \cdot 2WO_3]_{0.50}[Mo_{12}Co_{5.5}Fe_{3.0}Si_{1.5}K_{0.08}O_x]_1$.

1. Annular comparative shaped catalyst body VK1-1 (in process stages B), C), D) and F), there is an air atmosphere (26° C. and relative air humidity of 65%))

Process Stage A)

a) Production of a finely divided starting material A1 (as a source of the elements Bi and W).

In a 1.75 m³ stainless steel jacketed vessel whose temperature was controlled by water (temperature control water flowed through the intermediate space) (D (diameter)=1.3 m, h (height)=1.9 m) with an infinitely regulable beam stirrer (D=0.8 m, h=1.68 m), 214.7 kg of tungstic acid at 25° C. (74.1% by weight of W, H. C. Starck, D-38615 Goslar, purity>99.9% by weight of WO₃ after calcination at 750° C., 0.4 μm<$d_{50}$<0.8 μm) were stirred (70 rpm) in portions at 25° C. within 20 min into 780 kg of an aqueous bismuth nitrate in nitric acid solution at a temperature of 25° C. (11.2% by weight of Bi; free nitric acid 3 to 5% by weight; apparent density: 1.22 to 1.27 g/ml, prepared with nitric acid from bismuth metal from Sidech S.A., 1495 Tilly, Belgium, purity: >99.997% by weight of Bi, <7 mg/kg of Pb, <5 mg/kg of each of Ni, Ag, Fe, <3 mg/kg of each of Cu, Sb, and <1 mg/kg of each of Cd, Zn). The resulting aqueous mixture was then stirred at 25° C. for another 3 h and then spray dried.

The spray drying was effected in an FS 15 rotary disk spray tower from Niro A/S, DK-2860 Soeborg, in hot air cocurrent at a gas inlet temperature of 300±10° C., a gas outlet temperature of 100±10° C., a disk speed of 18 000 rpm, a throughput of 200 l/h, an air rate of 1800 m³ (STP)/h and a residence time of 2.2 minutes. The resulting spray powder had an ignition loss of 12.8% by weight (calcined at 600° C. for 3 h in a porcelain crucible (which had been calcined to constant weight at 900° C.) under air) and (at a dispersion pressure of 1.1 bar absolute) a $d_{50}$ of 28.0 μm ($d_{10}$=9.1 μm, $d_{90}$=55.2 μm). Table 1 which follows gives an overview of representative $d_x$ values of the spray powder in μm as a function of the absolute dispersion pressure employed in bar:

TABLE 1

|  | 2 bar | 1.5 bar | 1.2 bar | 1.1 bar |
|---|---|---|---|---|
| $d_{10}$ (μm) | 0.91 | 1.17 | 3.4 | 9.1 |
| $d_{50}$ (μm) | 5.8 | 8.5 | 19.7 | 28.0 |
| $d_{90}$ (μm) | 27.5 | 34.3 | 47.2 | 55.2 |

The resulting spray powder was subsequently converted to a paste with 16.7% by weight (based on the weight of spray powder) of water at 25° C. in a VIU-160 discharging kneader from AMK (Aachener Misch-und Knetfabrik, Peter Küpper GmbH & Co KG, 20 rpm) for 30 min, and extruded by means of a G 103-10/D7A-752K extruder from Bonnot Company (Uniontown, Ohio, USA, torque: ≤50 Nm) to extrudates of diameter 6 mm. These were cut into 6 cm sections, dried under air on a 3-zone belt drier (from Grenzebach BSH GmbH, D-36222 Bad Hersfeld) at a residence time of 120 min per zone at air temperatures of 90-95° C. (zone 1), 115° C. (zone 2) and 125° C. (zone 3), and then treated thermally at a temperature of approx. 830° C. (external temperature of the electrically heated rotary tube furnace) (calcined; in a rotary tube furnace with air flow (in countercurrent, pressure 0.3 mbar, capacity 1.54 $m^3$, internal diameter 0.7 m, slope 7 cm with length 4 m of the oven, wall thickness 8 mm, 200 $m^3$ (STP)/h of air, 50 kg/h of extrudate, speed: 1 rpm)). What is essential here in the exact setting of the calcination temperature is that it is oriented to the desired phase composition of the calcination product, but the calcined material, on the other hand, has a BET surface area of ≥0.2 $m^2$/g. What are desired here are the $WO_3$ (monoclinic) and $Bi_2W_2O_9$ (orthorhombic) phases; what is undesired is the presence of γ-$Bi_2WO_6$ (russellite). Should, therefore, after the calcination, the content of the compound γ-$Bi_2WO_6$ be more than 5 intensity % (calculated as the ratio of the intensity of the reflection of γ-$Bi_2WO_6$ in the X-ray powder diffractogram at $2\Theta=28.4°$ (CuKα radiation) to the intensity of the reflection of $Bi_2W_2O_9$ at $2\Theta=30.0°$), the preparation should be repeated and the calcination temperature or the residence time should be increased at the same calcination temperature until the limit is attained. The preformed calcined mixed oxide thus obtained was ground at 2500 rpm with a 500 BQ Biplex crossflow classifying mill from Hosokawa Alpine AG, D-86199 Augsburg, such that the $d_{50}$ value (measured at a dispersion pressure of 2.0 bar absolute) was 2.5 μm ($d_{10}$=1.1 μm, $d_{90}$=6.0 μm) and the BET surface area (DIN 66131, nitrogen adsorption) was 0.7 $m^2$/g.

The γ-$Bi_2WO_6$ content was 3 intensity %.

The millbase was then mixed in 20 kg portions in an inclined layer mixer (VIS type, capacity: 60 l, Aachener Misch-und Knetmaschinenfabrik) with mixing and cutting blades (mixing blade speed: 60 rpm, cutting blade speed: 3000 rpm) homogeneously with 0.5% by weight (based on the millbase) of finely divided hydrophobized $SiO_2$ (anticaking agent) from Degussa of the SIPERNAT® D17 type (tapped density 150 g/l; $d_{50}$ value of the $SiO_2$ particles (laser diffraction to ISO 13320-1) was 10 μm, the specific surface area (nitrogen adsorption to ISO 5794-1, Annex D) was 100 $m^2$/g) within 5 min.

b) Preparation of a Finely Divided Starting Material 2 from Different Sources Q

A solution A was prepared by, in a stainless steel 1.75 $m^3$ jacketed vessel whose temperature was controlled by water (temperature control water flowed through the intermediate space) (D=1.3 m, h=1.9 m) and which had an infinitely regulable beam stirrer (D=0.8 m, h=1.68 m), at 60° C. with stirring (70 rpm), metering 1.075 kg of an aqueous potassium hydroxide solution (47.5% by weight of KOH) at a temperature of 60° C. within one minute, and then, by means of a differential metering balance with a metering rate of 600 kg/h, 237.1 kg of ammonium heptamolybdate tetrahydrate (white crystals with a particle size d of <1 mm, 81.5% by weight of $MoO_3$, 7.0-8.5% by weight of $NH_3$, max. 150 mg/kg of alkali metals, H. C. Starck, D-38642 Goslar), into 660 l of water at 60° C., and stirring the resulting slightly cloudy solution at 60° C. for 60 min (70 rpm).

A solution B was prepared by initially charging a stainless steel 1.75 $m^3$ jacketed vessel whose temperature was controlled with water (temperature control water flowed through the intermediate space) (D=1.3 m, h=1.9 m) with an infinitely regulable beam stirrer (D=0.8 m, h=1.68 m), at 60° C., 282.0 kg of aqueous cobalt(II) nitrate in nitric acid solution at a temperature of 60° C. (pH (at 25° C. and 1 bar)=4, 12.5% by weight of Co, prepared with nitric acid from cobalt metal from MFT Metals & Ferro-Alloys Trading GmbH, D-41747 Viersen, purity, >99.6% by weight, <0.3% by weight of Ni, <100 mg/kg of Fe, <50 mg/kg of Cu), and metering thereto, with stirring (70 rpm), 142.0 kg of an iron(III) nitrate nonahydrate melt at 60° C. (13.8% by weight of Fe, <0.4% by weight of alkali metals, <0.01% by weight of chloride, <0.02% by weight of sulfate, Dr. Paul Lohmann GmbH, D-81857 Emmerthal). Subsequently, the mixture was stirred while maintaining at 60° C. for a further 30 minutes. Then, while maintaining at 60° C., solution B was discharged into the initially charged solution A within 10 minutes and stirred at 60° C. at 70 rpm for a further 15 minutes. Subsequently, as the Si source, 19.9 kg of a silica gel from Grace of the Ludox™ 50 type (50.1% by weight of $SiO_2$, density: 1.29 g/ml, pH 8.5 to 9.5, alkali metal content max. 0.5% by weight) were added to the resulting aqueous mixture which was then stirred at 60° C. at 70 rpm for a further 15 minutes.

Subsequently, spray drying was effected in hot air countercurrent in an FS-15 rotary disk spray tower from Niro A/S, DK-2860 Soeborg (gas inlet temperature: 350±10° C., gas outlet temperature: 140±5° C., disk speed: 16 000 rpm, throughput: 270 kg/h, air rate: 2100 $m^3$ (STP)/h, residence time: 1.9 minutes). The resulting spray powder had an ignition loss of 31.0% by weight (calcine under air at 600° C. for 3 h), a residual moisture content (water content) of 6.0% by weight (measured (as in all cases in this document) with the Smart System 5 instrument from CEM Corporation (3100 Smith Farm Road, PO Box 200, Matthews, N.C. 28106, USA) as the weight loss in the course of heating by means of microwaves (maximum power of the instrument: 300 W; analysis program: power: 45% of the maximum power, drying time: 3 min, no BIAS correction (instrument-specific), max. temperature (were this sample temperature to be attained, the instrument switches off automatically): 250° C., sample weight: 0.06-0.10 g)), a nitrogen content of 9.2% by weight, an ammonium content of 5.4% by weight and a $d_{50}$ (measured at a dispersion pressure of 2.0 bar absolute) of 36 μm ($d_{10}$=10 μm, $d_{90}$=72 μm).

c) Preparation of the Finely Divided Mixture M 110 kg of the finely divided starting material 2 were then initially charged in an inclined layer mixer manufactured from 1.4541 stainless steel (VIL type, capacity: 200 l, Aachener Misch-und Knetmaschinenfabrik) with mixing and cutting blades (mixing blade speed: 39 rpm, cutting blade speed: 3000 rpm), and were premixed for 1 min. Within 10 min, with continued mixing, finely divided starting material 1 was metered thereto via a star feeder in the amount required for a multielement oxide active material of the stoichiometry:

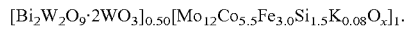
$[Bi_2W_2O_9 \cdot 2WO_3]_{0.50}[Mo_{12}Co_{5.5}Fe_{3.0}Si_{1.5}K_{0.08}O_x]_1$.

The mixing operation was then continued for a further 15 min in order to achieve intensive and complete homogenization (which is required to achieve a high activity and a high selectivity of acrolein formation of the later annular shaped catalyst bodies) (including the reformation of agglomerates which may form) of the two starting materials. Based on the aforementioned overall material, 1% by weight of TIMREX T44 graphite from Timcal AG ($d_{50}$=20.8 µm) were mixed in within a further 2 min to obtain the finely divided mixture M. The finely divided mixture M did not have any particles with a particle diameter $d^M$ of ≥160 µm.

Process Stage B)
Production of the Agglomerates A

The finely divided mixture M was then press agglomerated in a two-roller press manufactured from 1.4541 stainless steel of the K200/100 two-roller compactor type from Hosokawa Bepex GmbH in D-74211 Leingarten with concave (depth=2 mm), (transverse) fluted smoothing rollers (gap width: 2.8 mm, roller diameter: 20 cm, roller speed: 9 rpm, target pressing force: approx. 75 kN, maximum pressure P1:3.75 kN/cm²) to give slugs of width approx. 10 cm and height approx. 2.8 mm (agglomerates A).

Process Stage C)
Production of the Powders P/P*

The slugs were comminuted by means of a GBM-406 pinned roller crusher manufactured from 1.4541 stainless steel and a downstream MGR-803 impact sieving machine manufactured from 1.4541 stainless steel (both from Frewitt Maschinenfabrik AG, CH-1700 Fribourg) with a rotor and a Frewitt sieve with a mesh width (square meshes of rectangular wire) of 1 mm. Integrated vibrating sieves from Allgaier (oversize sieve width (relevant only in the case of a defective Frewitt sieve): 1.5 mm, undersize sieve width: 400 µm) with rubber ball knocking (rubber ball diameter=22 mm) were used to isolate a powder P whose particle diameter $d^P$ is 400 µm≤$d^P$≤1 mm. The quantitative distribution between the oversize, the desired powder P and the fines F (undersize) was <1% by weight: approx. 50% by weight: approx. 50% by weight. The fines F were recycled upstream of the two-roller compactor by means of suction conveying and press agglomerated again to slugs in a mixture M* with newly supplied finely divided mixture M.

To produce the annular shaped bodies V in process stage D), a further 2.5% by weight of the TIMREX T44 graphite from Timcal AG were added to the powder P in an S 5 belt screw mixer from Draiswerke GmbH in D-68305 Mannheim within 2 min, and the resulting mixture P* was transported by means of suction conveying to the tableting machine. In the mixture tableted in the tableting machine, the proportion by weight with $d^P$≥160 µm was 85% by weight (determination by sieve analysis; determination as in all corresponding sieve analyses in this document by sieving for 5 minutes at maximum amplitude with a test sieve of mesh size 160 µm and the AF 200 sieve apparatus from Retsch GmbH in 42781 Haan, Reinische Strasse 36), with a tapped density of the mixture of 1250 g/l (for determination, approx. 0.75 l of mixture is metered within approx. 90 s by means of a feeder (from Retsch, model DR 1000) and a powder funnel into a 1 l polymethylpentene measuring cylinder (from Nalgene, Buddenberg-catalog 95/96, order No. 9.274 927) disposed on a tamping volumeter (from JEL, model STAV 2003), and compacted with 700 taps for 3.08 min; the tapped density was then calculated as the quotient of mass introduced and volume occupied in the measuring cylinder) and a residual moisture content (a water content) of 5.7% by weight. The weight ratio of residual moisture content to weight loss at 450° C. (heat at 450° C. for 3 h in a porcelain crucible (which had been calcined to constant weight at 900° C.) under air) was 22%. $G^W$ was 28% by weight.

Process Stage D)
Production of the Annular Shaped Bodies V

Subsequently, the powder P* conveyed to the tableting machine was tableted in the same tableting machine (a PH 865 Korsch rotary press from Korsch) as in example II. of German Application 102008040093.9, at a speed of the tableting plate of approx. rpm under an air atmosphere to give annular shaped bodies V of geometry mm×3 mm×2 mm (external diameter×height×internal diameter) with a side crushing strength of 19 N. The main pressing force was approx. 4.2 kN. The maximum pressure P2 was 25.5 kN/cm². In order to prevent dust release, the tableting machine was provided with a suction system (300 to 400 m³ (STP)/h). The waste air was conducted through an HSL 900-8/8 SZ filter from Herding in D-92224 Amberg, which was cleaned periodically to obtain the filtercake consisting of solid particles FP.

Process Stage E)
Thermal Treatment of the Annular Shaped Bodies V to Obtain the Annular Comparative Shaped Catalyst Bodies VK1-1

For the final thermal treatment, in each case 1000 g of a representative mixed sample of the annular shaped bodies V produced as described were distributed homogeneously on 4 grids arranged alongside one another with a square base area of in each case 150 mm×150 mm (bed height: approx. 15 mm) in a forced air oven through which air flowed at 1000 l (STP)/h (from Heraeus Instruments GmbH, D-63450 Hanau, type: K 750/2) first at a heating rate of 80° C./h from room temperature (25° C.) to 185° C. This temperature was maintained for 1 h and then increased at a heating rate of 48° C./h to 225° C. The 225° C. was maintained for 2 h, before being increased to 270° C. at a heating rate of 120° C./h. This temperature was likewise maintained for 1 h before being increased to 464° C. at a heating rate of 60° C./h. This end temperature was maintained for 10 hours. This was followed by cooling to room temperature to obtain the annular comparative shaped catalyst bodies VK1-1 with a side crushing strength of 6.8 N and an apparent density of 1.92 g/ml.

In a subsequent undersize sieving with a stainless steel 1.4541 sieve with elongated holes (straight edge length: 20 mm, edge separation: 1.8 mm), based on the weight of the sieving material introduced to the sieving overall, an undersize fraction of 2.3% by weight was obtained.

Instead of performing the thermal treatment as described above, it can also be performed by means of a belt calcining apparatus as described in example 1 of DE-A 100 46 957 (the bed height in the decomposition (chambers 1 to 4) is, however, advantageously 42 mm with a residence time per chamber of 1.23 h, and, in the calcination (chambers 5 to 8), it is advantageously 130 mm at a residence time of 3.89 h). The chambers have a base area (with a uniform chamber length of 1.40 m) of 1.29 m² (decomposition) and 1.40 m² (calcination) and are flowed through from below through the coarse-mesh conveyer belt by 50-150 m³ (STP)/h of feed air preheated to 100° C. (decomposition) or 450° C. (calcination). In addition, the air is circulated by rotating ventilators (900 to 1500 rpm). Within the chambers, the deviation of the temperature from the target value in terms of time and space (typical values of zones 1-8 are: 140° C., 190° C., 220° C., 265° C., 380° C., 425° C., 460° C., 460° C.) is always ≤2° C. Beyond chamber 8 there advantageously follows a 2 m-long cooling zone at a controlled temperature of 70° C. (by means of water cooling in cooling ribs). Otherwise, the procedure is as described in example 1 of DE-A 100 46 957. The resulting comparative shaped catalyst bodies VK1-1 are suitable in the same way as catalysts for the partial oxidation of propylene to acrolein. They can also be conducted through a mm×20 mm sieve with elongated slots to remove agglomerates, and through one slotted sieve (preferably two slotted sieves) (1.8 mm×20 mm elongated slots) to remove fragments formed.

In an alternative embodiment, all process stages were repeated identically. After process stage D), the annular shaped bodies V obtained therein were conducted by means of an E.A. 36-2 vibrating sieving machine from Engelsmann AG in D-67059 Ludwigshafen am Rhein through a 1.4541 stainless steel slotted sieve (rectangular slots of length 30 mm and width 1.8 mm) and, as process stage F, separated into intact shaped bodies V$^+$ (approx. 98% by weight) as oversize and non-intact shaped bodies V$^-$ (approx. 2% by weight). Thermal treatment of the annular shaped bodies V$^+$ in a forced air oven, performed as already described, again afforded the comparative shaped catalyst bodies VK1-1. In a subsequent undersize sieving thereof with a 1.4541 stainless steel sieve with elongated holes (straight edge length: 20 mm, edge separation: 1.8 mm), based on the weight of the sieving material introduced to the sieving overall, only an undersize fraction of 0.2% by weight was obtained.

2. Annular shaped catalyst bodies K1-1 (in process stages B), C), D), F), and G), there was an air atmosphere (26° and relative air humidity of 65%))

The preparation process corresponded to that for preparing the comparative shaped catalyst bodies VK1-1, but with the following differences:
a) The shaped bodies V$^-$ removed in process stage F) were ground as process stage G), with a hammer mill from Hosokawa Alpine AG, D-86199 Augsburg (particle diameter 1 μm<d$^H$<100 μm; sieve analysis). The resulting finely divided aggregate H was stored intermediately in a closed collecting vessel and recycled from there by suction upstream of process stage B) and incorporated into the mixture M* with a proportion by weight of 20% by weight based on the overall weight).
b) The filtercake of solid particles FP obtained in process stage D) was collected in a closed collecting vessel and recycled from there by suction upstream of process stage B) and likewise incorporated into the mixture M* (with a proportion by weight of 2% by weight based on the total weight) and the mixture M* was press agglomerated to slugs.

In the mixture tableted with the tableting machine, the proportion by weight with d$^P$>160 μm was 79% by weight (determination by sieve analysis), at a tapped density of the mixture of 1300 g/l and a residual moisture content (a water content) of 6.5% by weight. The weight ratio of residual moisture contents to weight loss at 450° C. (heat at 450° C. for 3 h in a porcelain crucible (which had been calcined to constant weight at 900° C.) under air) was 25%. G$^W$ was 33% by weight. The side crushing strength of the resulting shaped bodies V was 22 N. The resulting shaped catalyst bodies K1-1 had a side crushing strength of 6.3 N and an apparent density of 1.93 g/ml.

3. Annular shaped catalyst bodies K1-2 (in process stages B), C), D), F) and G), there was an air atmosphere with elevated air humidity (31 and relative air humidity of 89%))

The production process corresponded to that for producing the shaped catalyst bodies K1-1, but with the difference of an elevated air humidity in process stages B), C), D), F) and G). In the mixture tableted with the tableting machine, the proportion by weight with d$^P$>160 μm was 83% by weight (determination by sieve analysis), at a residual moisture content (a water content) of 9.9% by weight. The weight ratio of residual moisture content to weight loss at 450° C. (heat at 450° C. for 3 h in a porcelain crucible (which had been calcined to constant weight at 900° C.) under air) was 35%. G$^W$ was 54% by weight. The side crushing strength of the resulting shaped bodies V was 23 N. The resulting shaped catalyst bodies K1-2 had a side crushing strength of 6.1 N and an apparent density of 1.91 g/ml.

4. Annular shaped catalyst bodies K1-3 (in process stages B), C), D), F) and G), there was an air atmosphere with elevated air humidity (31° and relative air humidity of 89%)

The production process corresponded to that for producing the shaped catalyst bodies K1-2, but with the difference that the finely divided aggregate H, before being recycled upstream of process stage B), had been stored intermediately in an open collecting vessel for 24 hours. In the mixture tableted with the tableting machine, the proportion by weight with d$^P$>160 μm was 86% by weight (determination by sieve analysis), with a residual moisture content (a water content) of 12.5% by weight. The weight ratio of residual moisture content to weight loss at 450° C. (heat at 450° C. for 3 h in a porcelain crucible (which had been calcined to constant weight at 900° C.) under air) was 42%. G$^W$ was 72% by weight. The side crushing strength of the resulting shaped bodies V was 24 N. The resulting shaped catalyst bodies K1-3 had a side crushing strength of 5.9 N and an apparent density of 1.90 g/ml.

II. Testing of the Annular Catalysts Produced in I. in a Heterogeneously Catalyzed Partial Gas Phase Oxidation of Propene to Acrolein A reaction tube (V2A steel; external diameter 21 mm, wall thickness 3 mm, internal diameter 15 mm, length 120 cm) was charged from the top downward in flow direction as follows:
Section 1: length approx. 30 cm
40 g of steatite spheres (C220 steatite from Ceram Tec) with a diameter of 1.5 to 2.0 mm as an inert preliminary bed (heating zone).
Section 2: length approx. 70 cm
100 g of the particular annular catalyst produced in I.
The temperature of the reaction tube was controlled in each case by means of a nitrogen-sparged salt bath (53% by weight of potassium nitrate, 40% by weight of sodium nitrite and 7% by weight of sodium nitrate).
The reactor was charged continuously with a starting reaction gas mixture (charge gas mixture of air, polymer grade propylene and nitrogen) of the following composition:
5% by volume of propene (polymer grade),
9.5% by volume of molecular oxygen and
85.5% by volume of molecular nitrogen.
At a volume flow of the starting reaction gas mixture (whose inlet temperature into the reaction tube was approx. 30° C.) of 100 l (STP)/h (5 l (STP)/h of propene (polymer grade)) conducted into the reaction tube, the reaction tube was thermostated by varying the salt bath temperature T$^S$ (° C.) in all cases such that the propene conversion C$^P$ (mol %) in single pass of the charge gas mixture through the reaction tube was continuously approx. 95 mol %.

Table 2 which follows shows (based in each case on a single pass of the reaction gas mixture through the reaction tube) the exact propylene conversion C$^P$ present after an operating time of 60 h for the particular catalyst charge of the reaction tube at the particular temperature T$^S$, the corresponding selectivity $S^{AC}$ of acrolein formation (mol %), and the selectivity $S^{AC+AA}$ of overall formation of acrolein and acrylic acid (mol %), which is essential in the case of a partial oxidation of the acrolein formed to acrylic acid performed in a downstream reaction stage.

TABLE 2

| Catalyst | $T^S$ (° C.) | $C^P$ (mol %) | $S^{AC}$ (mol %) | $S^{AC+AA}$ (mol %) |
|---|---|---|---|---|
| VK1-1 | 331 | 95.3 | 86.3 mol % | 93.9 mol % |
| K1-1 | 329 | 95.2 | 85.6 mol % | 93.5 mol % |
| K1-2 | 332 | 95.1 | 85.1 mol % | 93.3 mol % |
| K1-3 | 335 | 95.1 | 84.3 mol % | 92.6 mol % |

In a surprising manner, the inventive recycling in the course of production of the annular catalysts, especially in the case of $S^{AC+AA}$, leads only to marginal losses which, at a low residual moisture content (low water content) of the recycled material and hence a low residual moisture content and a low $G^W$ of the shaped bodies V, vary toward the limit of measurement accuracy.

III. Production of Annular Shaped Catalyst Bodies K and Annular Comparative Shaped Catalyst Bodies VK, Each of Whose Multielement Oxide Active Materials have the Following Stoichiometry:

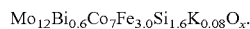

$Mo_{12}Bi_{0.6}Co_7Fe_{3.0}Si_{1.6}K_{0.08}O_x$.

1. Annular comparative shaped catalyst bodies VK2-1 (in process stages B), C), D) and F), there was an air atmosphere (26° C. and relative air humidity of 60%))

Process Stage A)
Production of the Finely Divided Mixture M from Different Sources Q A solution A was prepared by, in a stainless steel 1.75 m³ jacketed vessel whose temperature was controlled by water (temperature control water flowed through the intermediate space) (D=1.3 m, h=1.9 m) and which had an infinitely regulable beam stirrer (D=0.8 m, h=1.68 m), at 60° C. with stirring (70 rpm), metering 0.62 kg of an aqueous potassium hydroxide solution (47.5% by weight of KOH) at a temperature of 25° C. within one minute, and then, by means of a differential metering balance with a metering rate of 600 kg/h, 139.7 kg of ammonium heptamolybdate tetrahydrate (white crystals with a particle size d of <1 mm, 81.5% by weight of $MoO_3$, 7.0-8.5% by weight of $NH_3$, max. 150 mg/kg of alkali metals, H. C. Starck, D-38642 Goslar), into 432 l of water at 65° C., and stirring the resulting solution at 60° C. for 90 min (70 rpm).

A solution B was prepared by initially charging a stainless steel 1.75 m³ jacketed vessel whose temperature was controlled with water (temperature control water flowed through the intermediate space) (D=1.3 m, h=1.9 m) with an infinitely regulable beam stirrer (D=0.8 m, h=1.68 m), at 60° C., 217.5 kg of aqueous cobalt(II) nitrate in nitric acid solution at a temperature of 60° C. (pH=4 (25° C., 1 atm), 12.5% by weight of Co, prepared with nitric acid from cobalt metal from MFT Metals & Ferro-Alloys Trading GmbH, D-41747 Viersen, purity, >99.6% by weight, <0.3% by weight of Ni, <100 mg/kg of Fe, <50 mg/kg of Cu), and metering thereto, with stirring (70 rpm), 80.0 kg of an iron(III) nitrate nonahydrate melt at 60° C. (13.8% by weight of Fe, <0.4% by weight of alkali metals, <0.01% by weight of chloride, <0.02% by weight of sulfate, Dr. Paul Lohmann GmbH, D-81857 Emmerthal). Subsequently, the mixture was stirred while maintaining at 60° C. for a further 30 minutes. Then, with continued stirring and while maintaining this temperature, 74.5 kg of aqueous bismuth nitrate in nitric acid solution (11.1% by weight of Bi; free nitric acid 3 to 5% by weight; apparent density: 1.22 to 1.27 g/ml, prepared with nitric acid from bismuth metal from Sidech S. A., 1495 Tilly, Belgium, purity: >99.997% by weight of Bi, <7 mg/kg of Pb, <5 mg/kg each of Ni, Ag, Fe, <3 mg/kg each of Cb, Su, and <1 mg/kg each of Cd, Zn) were stirred in, and then stirred while maintaining at 60° C. for another 30 minutes. Then, while maintaining at 60° C. and with continued stirring, solution B was discharged into the initially charged solution A within 15 minutes, the vessel was rinsed with 5 l of water and the suspension formed was stirred at 60° C. at 70 rpm for a further 15 minutes. Subsequently, as the Si source, 10 l of a silica gel from Grace of the Ludox™ 50 type (49.1% by weight of $SiO_2$, density: 1.29 g/ml, pH 8.5 to 9.5, alkali metal content max. 0.5% by weight) were added to the resulting aqueous mixture which was then stirred at 60° C. at 70 rpm for a further 15 minutes.

Subsequently, spray drying was effected in hot air countercurrent in an FS-15 rotary disk spray tower from Niro A/S, DK-2860 Soeborg (gas inlet temperature: 350±10° C., gas outlet temperature: 140±5° C., disk speed: 18 000 rpm, throughput: 270 kg/h, air rate: 2100 m³ (STP)/h, residence time: 1.9 minutes). The resulting spray powder had an ignition loss of 30.0% by weight (calcine under air at 600° C. for 3 h), a residual moisture content of 6.5% by weight and a $d_{50}$ (measured at a dispersion pressure of 2.0 bar absolute) of 27 µm ($d_{10}$=4.7 µm, $d_{90}$=59 µm).

100 kg of this spray powder and 1 kg of Asbury 3160 graphite (from Asbury Graphite Mills, Inc. New Jersey 08802, USA) with a $d_{50}$ of 123 µm were then mixed in an inclined layer mixer (VIL type, capacity: 200 l, Aachener Misch-und Knetmaschinenfabrik) with mixing but no cutting blades (mixing blade speed: 39 rpm) for 5 minutes to obtain the finely divided mixture M. The finely divided mixture M comprises less than 1% by weight of particles with a particle diameter $d^M$ of ≥160 µm.

Process Stage B)
Production of the Agglomerates A

The finely divided mixture M was then press agglomerated in a two-roller press manufactured from 1.4541 stainless steel of the K200/100 two-roller compactor type from Hosokawa Bepex GmbH with concave (depth=2 mm), (transverse) fluted smoothing rollers (gap width: 2.8 mm, roller speed: 10 rpm, target pressing force: approx. 35 kN, maximum pressure P1: 1.75 kN/cm²) to give slugs of width approx. 10 cm and height approx. 2.8 mm (agglomerates A).

Process Stage C)
Production of the Powders P/P*

The slugs were comminuted by means of a GBM-406 pinned roller crusher manufactured from 1.4541 stainless steel and a downstream MGR-803 impact sieving machine manufactured from 1.4541 stainless steel (both from Frewitt Maschinenfabrik AG, CH-1700 Fribourg) with a rotor and a Frewitt sieve with a mesh width (square meshes of rectangular wire) of 1 mm. Integrated vibrating sieves from Allgaier (oversize sieve width (relevant only in the case of a defective Frewitt sieve): 1.5 mm, undersize sieve width: 200 µm) with rubber ball knocking (rubber ball diameter=22 mm) were used to isolate a powder P whose particle diameter $d^P$ was 200 µm≤$d^P$≤1 mm. The quantitative distribution between the oversize, the desired powder P and the fines (undersize) was <1% by weight: approx. 60% by weight: approx. 40% by weight. The fines F were recycled upstream of the two-roller compactor by means of suction conveying and press agglomerated again to slugs in a mixture M* with newly supplied finely divided mixture M.

To produce the annular shaped bodies V in process stage D), a further 2% by weight of the Asbury 3160 graphite were added to the powder P in an S5 turbulent mixer from Draiswerke GmbH in D-68305 Mannheim within 2 min, and the resulting powder P* was transported by means of suction conveying to the tableting machine. In the mixture tableted in the tableting machine, the proportion by weight with $d^P>160$ μm was 78.5% by weight (determination by sieve analysis) and the residual moisture content was 6.9% by weight. The weight ratio of residual moisture content to weight loss at 450° C. (heat at 450° C. for 3 h in a porcelain crucible (which had been calcined to constant weight at 900° C.) under air) was 23%. $G^W$ was 30% by weight.

Process Stage D)
Production of the Annular Shaped Bodies V

Subsequently, the powder P* conveyed to the tableting machine was tableted in the same tableting machine (a Kilian RX 73 rotary press from Kilian, D-50735 Cologne) as in example III. of German Application 102008040093.9, under an air atmosphere to give annular shaped bodies V of geometry 5 mm×3 mm×2 mm (external diameter×height×internal diameter) with a side crushing strength of 19 N. The maximum pressure P2 was 21.6 kN/cm². The rotary press table is equipped with exchangeable dies. In order to prevent dust release, the tableting machine was provided with a suction system (300 to 400 m³ (STP)/h). The waste air was conducted through an HSL 900-8/8 SZ filter from Herding in D-92224 Amberg, which was cleaned periodically to obtain the filtercake consisting of solid particles FP.

Process Stage E)
Thermal Treatment of the Annular Shaped Bodies V to Obtain the Annular Comparative Shaped Catalyst Bodies VK2-1

For the final thermal treatment, in each case 1000 g of a representative mixed sample of the shaped bodies V produced as described were distributed homogeneously on 4 grids arranged alongside one another with a square base area of in each case 150 mm×150 mm (bed height: approx. 15 mm) in a forced air shaft oven with an air flow of 1200 l (STP)/h (from Nabertherm GmbH, Bahnhofstrasse 20, D-28865 Lilienthal/Bremen, S60/65A type with Siemens SPS7 and H 1700 operating panel, and internal temperature regulation) first from room temperature (25° C.) to 130° C. within 72 min. This temperature was maintained for 72 min and then increased to 190° C. within 36 min. After a hold time of 72 min, the oven was heated to 220° C. within 36 min. The 220° C. were maintained for 72 min, before the temperature was increased to 265° C. within 36 min. This temperature was likewise maintained for 72 min, before it was increased to 380° C. within 93 min. After a hold time of 187 min, the oven was heated to 430° C. within 93 min and then this temperature, after a further hold time of 187 min, was increased to 500° C. within 93 min. This end temperature was maintained for 467 min. Then the oven was cooled to room temperature and the annular comparative shaped catalyst bodies VK2-1 were obtained with a side crushing strength of 6.3 N.

In a subsequent undersize sieving with a stainless steel 1.4541 sieve with elongated holes (straight edge length: 20 mm, edge separation: 1.8 mm), based on the weight of the sieving material introduced to the sieving overall, an undersize fraction of 3.4% by weight was obtained.

Instead of performing the thermal treatment as described above, it can also be performed by means of a belt calcining apparatus as described in example 1 of DE-A 100 46 957 (the bed height in the decomposition (chambers 1 to 4) is, however, advantageously 32 mm with a residence time per chamber of 1.8 h, and, in the calcination (chambers 5 to 8), it is advantageously 77 mm at a residence time of 4.7 h). The chambers have a base area (with a uniform chamber length of 1.40 m) of 1.29 m² (decomposition) and 1.40 m² (calcination) and are flowed through from below through the coarse-mesh conveyer belt by 50-150 m³ (STP)/h of feed air preheated to 100° C. (decomposition) or 470° C. (calcination). In addition, the air is circulated by rotating ventilators (900 to 1400 rpm). Within the chambers, the deviation of the temperature from the target value in terms of time and space (typical values of zones 1-8 are: 150° C., 190° C., 220° C., 265° C., 380° C., 430° C., 500° C., 500° C.) is always ≤2° C. Beyond chamber 8 there advantageously follows a 2 m-long cooling zone at a controlled temperature of 90° C. Otherwise, the procedure is as described in example 1 of DE-A 100 46 957. The resulting comparative shaped catalyst bodies VK2-1 are suitable in the same way as catalysts for the partial oxidation of propylene to acrolein. They can also be conducted through a 5 mm×20 mm sieve with elongated slots to remove agglomerates, and through one slotted sieve (preferably two slotted sieves) (1.8 mm×20 mm elongated slots) to remove calcined fragments.

In an alternative embodiment, all process stages were repeated identically. After process stage D), the annular shaped bodies V obtained therein were conducted by means of an E.A. 36-2 vibrating sieving machine from Engelsmann AG in D-67059 Ludwigshafen am Rhein through a 1.4541 stainless steel slotted sieve (rectangular slots of length 30 mm and width 1.8 mm) and, as process stage F, separated into intact shaped bodies V⁺ (approx. 97% by weight) as oversize and non-intact shaped bodies V⁻ (approx. 3% by weight). Thermal treatment of the annular shaped bodies V⁺ in a forced air oven, performed as already described, again afforded the comparative shaped catalyst bodies VK2-1. In a subsequent undersize sieving thereof with a 1.4541 stainless steel sieve with elongated holes (straight edge length: 20 mm, edge separation: 1.8 mm), based on the weight of the sieving material introduced to the sieving overall, only an undersize fraction of 0.4% by weight was obtained.

2. Annular shaped catalyst bodies K2-1 (in process stages B), C), D), F), and G), there was an air atmosphere (26° and relative air humidity of 60%))

The preparation process corresponded to that for preparing the comparative shaped catalyst bodies VK2-1, but with the following differences:

a) The shaped bodies V⁻ removed in process stage F) were ground as process stage G), with a hammer mill from Hosokawa Alpine AG, D-86199 Augsburg (particle diameter 1 μm<$d^H$<100 μm; sieve analysis). The resulting finely divided aggregate H was stored intermediately in a closed collecting vessel and recycled from there by suction upstream of process stage B) and incorporated into the mixture M* (with a proportion by weight of 20% by weight based on the overall weight).

b) The filtercake of solid particles FP obtained in process stage D) was collected in a closed collecting vessel and recycled from there by suction upstream of process stage B) and likewise incorporated into the mixture M* (with a proportion by weight of 2% by weight based on the total weight) and the mixture M* was press agglomerated to slugs.

In the mixture tableted with the tableting machine, the proportion by weight with $d^F \geq 160$ μm was 77.5% by weight and the residual moisture content (the water content) was 7.9% by weight. The weight ratio of residual moisture contents to weight loss at 450° C. (heat at 450° C. for 3 h in a porcelain crucible (which had been calcined to constant weight at 900° C.) under air) was 26%. $G^W$ was 35% by weight. The side crushing strength of the resulting shaped bodies V was 20 N. The resulting shaped catalyst bodies K2-1 had a side crushing strength of 6.1 N.

3. Annular shaped catalyst bodies K2-2 (in process stages B), C), D), F) and G), there was an air atmosphere with elevated air humidity (32° and relative air humidity of 91%))

The production process corresponded to that for producing the shaped catalyst bodies K2-1, but with the difference of an elevated air humidity in process stages B), C), D), F) and G). In the mixture tabletted with the tabletting machine, the proportion by weight with $d^P>160$ μm was 95.7% by weight (determination by sieve analysis), at a residual moisture content (a water content) of 11.5% by weight. The weight ratio of residual moisture content to weight loss at 450° C. (heat at 450° C. for 3 h in a porcelain crucible (which had been calcined to constant weight at 900° C.) under air) was 35%. $G^W$ was 54% by weight. The side crushing strength of the resulting shaped bodies V was 22 N. The resulting shaped catalyst bodies K2-2 had a side crushing strength of 5.9 N.

4. Annular shaped catalyst bodies K2-3 (in process stages B), C), D), F) and G), there was an air atmosphere with elevated air humidity (32° and relative air humidity of 91%)

The production process corresponded to that for producing the shaped catalyst bodies K2-2, but with the difference that the finely divided aggregate H, before being recycled upstream of process stage B), had been stored intermediately in an open collecting vessel for 24 hours. In the mixture tabletted with the tabletting machine, the proportion by weight with $d^P \geq 160$ μm was 98.8% by weight (determination by sieve analysis; lower decomposition or reagglomeration as a result of elevated residual moisture content), with a residual moisture content (a water content) of 14.1% by weight. The weight ratio of residual moisture content to weight loss at 450° C. (heat at 450° C. for 3 h in a porcelain crucible (which had been calcined to constant weight at 900° C.) under air) was 41%. $G^W$ was 69% by weight. The side crushing strength of the resulting shaped bodies V was 24 N. The resulting shaped catalyst bodies K2-3 had a side crushing strength of 5.5 N.

5. Annular shaped catalyst bodies K2-4 (in process stages B), C), D), F) and G), there was an air atmosphere with elevated air humidity (32° and relative air humidity of 92%) and the proportion of the recycled fines F is increased)

The production process corresponded to that for producing the shaped catalyst bodies K2-2, but with the difference that the mesh size of the undersize vibrating sieve in process stage C) was 400 μm. This increased the proportion by weight of the fines F to approx. 70% by weight. The proportion by weight with $d^P \geq 160$ μm was 98.9% by weight (determination by sieve analysis; relatively low decomposition or reagglomeration as a result of elevated residual moisture content), at a residual moisture content (a water content) of 13.9% by weight. The weight ratio of residual moisture content to weight loss at 450° C. (heat at 450° C. for 3 h in a porcelain crucible) which had been calcined to constant weight at 900° C.) under air) was 41%. $G^W$ was 69% by weight. The side crushing strength of the resulting shaped bodies V was 23 N. The resulting shaped catalyst bodies K2-4 had a side crushing strength of 5.7 N.

IV. Testing of the Annular Catalyst Produced in III. in a Heterogeneously Catalyzed Partial Gas Phase Oxidation of Propene to Acrolein The catalytic testing was effected as described for the annular catalysts under II. Table 3 below shows the results achieved in a manner corresponding to table 2.

TABLE 3

| Catalysts | $T^S$ (° C.) | $C^P$ (mol %) | $S^{AC}$ (mol %) | $S^{AC+AA}$ (mol %) |
|---|---|---|---|---|
| VK2-1 | 319 | 95.0 | 91.0 | 95.7 |
| K2-1 | 318 | 95.0 | 90.8 | 95.5 |
| K2-2 | 319 | 95.1 | 90.6 | 95.1 |
| K2-3 | 321 | 95.1 | 89.5 | 93.8 |
| K2-4 | 319 | 95.0 | 90.0 | 94.4 |

In a surprising manner, the inventive recycling in the course of preparation of the annular catalysts, especially in the case of $S^{AC+AA}$, leads only to marginal losses which, at a low residual moisture content (low water content) of the recycled material and hence a low residual moisture content and a low $G^W$ of the shaped bodies V, vary toward the limit of measurement accuracy.

V. Production of Annular Shaped Catalyst Bodies K and Annular Comparative Shaped Catalysts Bodies VK, Each of Whose Multielement Oxide Active Materials has the Following Stoichiometry:

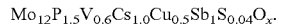

$Mo_{12}P_{1.5}V_{0.6}Cs_{1.0}Cu_{0.5}Sb_1S_{0.04}O_x$.

1. Annular comparative shaped catalyst bodies VK3-1 (in process stages B), C), D) and F), there was an air atmosphere (27° C. and relative air humidity of 71%))

Process Stage A)
Production of the Finely Divided Mixture M from Different Sources Q A 1.75-m³ stainless steel jacketed vessel whose temperature was controlled by water (temperature control water flowed through the intermediate space) (D=1.3 m, h=1.9 m) and which had an infinitely regulable beam stirrer (D=0.8 m, h=1.68 m) was initially charged with 619 l of water heated to 45° C. and stirred at 70 revolutions per minute (rpm) during the subsequent steps. Within approx. 40 minutes, 537.5 kg of ammonium heptamolybdate tetrahydrate having a temperature of 25° C. ((NH$_4$)$_6$Mo$_7$O$_{24}$·4H$_2$O (81% by weight of MoO$_3$, 8% by weight of NH$_3$, ≤50 ppm by weight of Na and ≤100 ppm by weight of K) were metered thereto. In the course of this, the temperature of the solution fell to 37° C. In order to ensure reliable dissolution of the ammonium heptamolybdate, the mixture was stirred for another 15 minutes after the end of the metered addition, in the course of which the temperature of 37° C. was maintained. At the same temperature, by means of a differential metering balance 17.82 kg of ammonium metavanadate (NH$_4$VO$_3$, 77% by weight of V$_2$O$_5$, 14.5% by weight of NH$_3$, ≤150 ppm by weight of Na and ≤500 ppm by weight of K) (each at 25° C.) were then metered in within 3 minutes. The mixture was stirred for a further 2 minutes. Then, within one minute, a colorless clear solution at 60° C., which had been prepared in a separate dissolution vessel (stirred 0.20-m³ stainless steel jacketed vessel (D=0.7 m, h=0.78 m)), of 49.6 kg of cesium nitrate (CsNO$_3$ with 72% by weight of Cs$_2$O and ≤50 ppm by weight of Na, ≤100 ppm by weight of K, ≤10 ppm by weight of Al and ≤20 ppm by weight of Fe, dissolution time approx. 30 min, during the subsequent metered addition, the reservoir vessel containing CsNO$_3$ solution was not stirred) in 106 l of water was added via a pipe stub (D=25 mm). In the course of this, the temperature of the resulting suspension rose to 39° C. After stirring for a further minute, within a further minute, from a 310 l reservoir vessel made of 1.4571 steel, via a pipe stub (D=25 mm), 31.66 l of 75% by weight phosphoric acid (density at 25° C. and 1 atm: 1.57 g/ml, viscosity at 25° C. and 1 atm: 0.147 cm²/S) were metered in. Owing to the exothermic reaction, the temperature rose in the course of this to 42°

C. The mixture was stirred again for another one minute. Then, within a minute, 1.34 kg of ammonium sulfate (($NH_4$)$_2$ $SO_4$ (>99% by weight)) were stirred in and the mixture was stirred for 1 further minute. During this, the warm water was blown out of the jacket of the mixing tank. At the same temperature, via a metering balance, 37.04 kg of antimony trioxide ($Sb_2O_3$, particle diameter $d_{50}$=approx. 2 μm, crystal structure according to XRD: >75% senarmontite, <25% valentinite, purity: >99.3% by weight, ≤0.3% by weight of $As_2O_3$, ≤0.3% by weight of PbO and ≤300 ppm by weight of FeO) were added within 3 minutes (commercially available as Triox White, Code No. 639000 from Antraco, D-10407 Berlin). The stirrer speed was then reduced from 70 to 50 rpm. Subsequently, the stirred suspension was heated by means of steam in the jacket in a linear manner to 95° C. within 30 minutes. At this temperature and 50 rpm, 51.64 kg of copper nitrate solution (aqueous Cu($NO_3$)$_2$-solution with 15.6% by weight of Cu) were added from a stainless steel reservoir vessel within 4 minutes. After stirring at 95° C. for a further 56 minutes, the stirrer speed was reduced further from 50 to 35 rpm. Subsequently, the entire suspension was discharged within 4 minutes into a spray tower reservoir vessel (1.75-$m^3$ stainless steel jacketed vessel (D=1.3 m, h=1.9 m) with an infinitely regulable beam stirrer (D=0.8 m, h=1.68 m)) blanketed with 10 $m^3$ (STP)/h of nitrogen, heated to 85° C. and stirred at 35 rpm, and rinsed with 20 l of water (25° C.) (later, cleaning was effected with 5 to 25% by weight aqueous $NH_3$ solution). From this reservoir vessel, the suspension was spray-dried in an FS-15 rotary disk spray tower from Niro A/S, DK-2860 Soeborg in hot air cocurrent with an inlet temperature of 300° C., an outlet temperature of 110° C., a disk speed of 18 000 rpm, a throughput of 270 kg/h, an air rate of 1800 $m^3$ (STP)/h and a residence time of 2.2 minutes within 3.5 h, and the resulting spray powder had an ignition loss (at 500° C. for 1 h in air) of 17.2% by weight and a $d_{50}$ of 35.9 μm ($d_{10}$=14.3 μm, $d_{90}$=65.6 μm, measured at a dispersion pressure of 2 bar absolute).

The spray powder was mixed in an inclined layer mixer (VIL type, capacity: 200 l, Aachener Misch-und Knetmaschinenfabrik) with mixing and cutting blades (mixing blade speed: 39 rpm, cutting blade speed: 3000 rpm) with 1.5% by weight of TIMREX T44 graphite ($d_{50}$=20.8 μm) from Timcal AG within 9 minutes to obtain the finely divided mixture M. The finely divided mixture M did not comprise any particles with a particle diameter $d^M$>160 μm.
Process Stage B)
Production of the Agglomerates A The finely divided mixture M was then press agglomerated in a two-roller press manufactured from 1.4541 stainless steel of the K200/100 two-roller compactor type from Hosokawa Bepex GmbH, D-74211 Leingarten with concave (depth=2 mm), fluted smoothing rollers (gap width: 2.8 mm, roller diameter: 20 cm, roller speed: 13 rpm, target pressing force: approx. 30 kN, maximum pressure P11: 1.5 kN/$cm^2$) to give slugs of width approx. 10 cm and height approx. 2.8 mm (agglomerates A).
Process Stage C)
Production of the Powders P/P*

The slugs were comminuted by means of a GBM-406 pinned roller crusher manufactured from 1.4541 stainless steel and a downstream MGR-803 impact sieving machine manufactured from 1.4541 stainless steel (both from Frewitt Maschinenfabrik AG, CH-1700 Fribourg) with a rotor and a Frewitt sieve with a mesh width (square meshes of rectangular wire) of 1 mm. Integrated vibrating sieves from Allgaier (oversize sieve width (relevant only in the case of a defective Frewitt sieve): 1.25 mm, undersize sieve width: 400 μm) with rubber ball knocking (rubber ball diameter=22 mm) were used to isolate a powder P whose particle diameter $d^P$ was 400 μm≤$d^P$≤1 mm. The quantitative distribution between the oversize, the desired powder P and the fines (undersize) was <1% by weight: approx. 55% by weight: approx. 45% by weight. The fines F were recycled upstream of the two-roller compactor by means of suction conveying and press agglomerated again to slugs in a mixture M* with newly supplied finely divided mixture M. The target pressing force value in process stage B) was regulated under closed-loop control so as to establish a tapped density of the powder P between 1350 and 1410 g/l.

To produce the annular shaped bodies V in process stage D), a further 1% by weight of the TIMREX T44 graphite from Timcal AG were added to the powder in an S5 belt screw mixer from Draiswerke GmbH in D-68305 Mannheim within 2 min, and the resulting mixture P* was transported by means of suction conveying to the tableting machine. In the mixture tableted in the tableting machine, the proportion by weight with $d^P$≥160 μm was 84% by weight (determination by sieve analysis) and the residual moisture content was 3.9% by weight. The weight ratio of residual moisture content to weight loss at 450° C. (heat at 450° C. for 3 h in a porcelain crucible (which had been calcined to constant weight at 900° C.) under air) was 24%. $G^W$ was 32% by weight.
Process Stage D)
Production of the Annular Shaped Bodies V Subsequently, the powder P* conveyed to the tableting machine was tableted in the same tableting machine (a PH 865 Korsch rotary press from Korsch) as in example IV. of German Application 102008040093.9, at a speed of the tableting plate of approx. rpm under an air atmosphere to give annular shaped bodies V of geometry 7 mm×7 mm×3 mm (external diameter×height×internal diameter) with a side crushing strength of 37±2 N. The main pressing force was approx. 3-5 kN. The maximum pressure P2 was 16 kN/$cm^2$. In order to prevent dust release, the tableting machine was provided with a suction system (300 to 400 $m^3$ (STP)/h). The waste air was conducted through an HSL 900-8/8 SZ filter from Herding in D-92224 Amberg, which was cleaned periodically to obtain the filtercake consisting of solid particles FP.
Process Stage E)
Thermal Treatment of the Annular Shaped Bodies V to Obtain the Annular Comparative Shaped Catalyst Bodies VK3-1

The thermal treatment was effected in two directly coupled belt calciners connected in series (the output of the first formed the input of the second belt calciner), as described in detail in DE-A 100 46 957 (the different zones of a belt calciner communicate on the gas side), each of which comprised 4 heating zones (chambers). The chambers possessed a base area (at a uniform chamber length of 1.40 m) of 1.29 $m^2$ (decomposition: 1st belt calciner) and 1.40 $m^2$ (calcination: 2nd belt calciner), and feed air preheated to 150° C. (decomposition) or 320° C. (calcination) flowed through the coursemesh conveyor belt from the bottom. This air was circulated in the chambers additionally by rotating ventilators. The characteristic parameters for the operation of the two belt calciners are summarized in table 5. In the 1st belt calciner (belt width=92 cm), the ammonium salts present in the geometric shaped bodies V were decomposed ("salt decomposition"). The concentration of the $NH_3$ released here was monitored continuously in all 4 heating zones of the 1st belt calciner by means of FTIR spectroscopy (Nicolet "Impact" spectrometer, stainless steel IR cell with $CaF_2$ window, path length 10 cm, heating to 120° C., determination of the concentration with reference to the intensity of the band at 3333 $cm^{-1}$). The measurements are likewise reported in table 5. The temperatures in zones 2 to 4 of the 1st belt calciner influence (together with the temperatures in the 2nd belt calciner) the residual ammonium content of the resulting annular comparative shaped catalyst bodies VK3-1 (but they do not influence the proportion therein of orthorhombic $MoO_3$). At a belt speed of 2.3 cm/min, the bed height in the 1st belt calciner was 50 mm. In the 2nd belt calciner, the end calcination of the geometric shaped bodies V. was effected. Analogously to the 4 heating zones of the 1st belt calciner, the first two zones in the 2nd belt calciner were monitored for the ammonia released. The temperatures in zones 6 to 8 served primarily as control parameters for the proportion of orthorhombic $MoO_3$ in the resulting annular comparative shaped catalyst bodies VK3-1, but also influenced the residual ammonium content thereof. In the 2nd belt calciner (belt width=100 cm), the belt speed was 1.0 cm/min, so as to result in a bed height of 105 mm. To remove agglomerates, the annular comparative shaped catalyst bodies VK3-1 thus obtained were also conducted through a slotted sieve with 9 mm (edge separation)×20 mm (edge lengths) elongated holes and, for the purpose of undersize sieving, through two slotted sieves with elongated holes (in each case 6 mm (edge separation)×20 mm (edge length)). The undersize fraction obtained was, based on the total amount of sieving material introduced, 23% by weight.

The annular comparative shaped catalyst bodies VK3-1 had a side crushing strength of N, an ammonium content (determined by Kjeldahl titration) of 0.52% by weight of $NH_4$, and an $MoO_3$ content of 2.1 intensity %. The latter is calculated as the ratio of the intensity (the definition of the intensity of a reflection in the X-ray diffractogram is always based in this document on the definition laid down in DE-A 198 35 247, and also in DE-A 100 51 419 and in DE-A 100 46 672) of the (021)$MoO_3$ reflection at $2\Theta=27.3°$ to the intensity of the (222) reflection of the heteropoly compound at $2\Theta=26.5°$ in the X-ray powder diffractogram (with Cu-Kα radiation).

In an alternative embodiment, all process stages were repeated identically. After process stage D), the annular shaped bodies V obtained therein were conducted by means of an E.A. 36-2 vibrating sieving machine from Engelsmann AG in D-67059 Ludwigshafen am Rhein through a 1.4541 stainless steel slotted sieve (rectangular slots of length 20 mm and width 5 mm) and, as process stage F, separated into intact shaped bodies $V^+$ (approx. 82% by weight) as oversize and non-intact shaped bodies $V^-$ (approx. 18% by weight). Thermal treatment of the annular shaped bodies $V^+$ in the two belt calciners connected in series, performed as already described, again afforded the annular comparative shaped catalyst bodies VK3-1. In a subsequent undersize sieving thereof with two 1.4541 stainless steel sieves with elongated holes (straight edge length: 20 mm, edge separation: 6 mm), only an undersize fraction of 5.2% by weight was obtained, based on the weight of the sieving material introduced overall to the sieving.

2. Annular shaped catalyst bodies K3-1 (in process stages B), C), D), F) and G), there was an air atmosphere (27° and relative air humidity of 71%))

The production process corresponded to that for preparing the comparative shaped catalyst bodies VK3-1, but with the following differences:

a) The shaped bodies $V^-$ removed in process stage F) were ground, as process stage G), with a hammer mill from Hosokawa Alpine AG, D-86199 Augsburg (particle diameter 1 μm<$d^H$<100 μm; sieve analysis). The resulting finely divided aggregate H was stored intermediately in a closed collecting vessel and recycled from there by suction upstream of process stage B), and incorporated into the mixture M* (with a proportion by weight of 20% by weight based on the total weight).

b) The filtercake of solid particles FP obtained in process stage D) was collected in a closed collecting vessel and recycled from there by suction upstream of process stage B), and likewise incorporated into the mixture M* (with a proportion by weight of 2% by weight based on the total weight), and the mixture M* was press agglomerated to slugs.

In the mixture tabletted with the tabletting machine, the proportion by weight with $d^P \geq 160$ μm was 80% by weight, and the residual moisture content (the water content) was 4.1% by weight. The weight ratio of residual moisture content to weight loss at 450° C. (heat at 450° C. for 3 h in a porcelain crucible (which had been calcined to constant weight at 900° C.) under air) was 26%. $G^W$ was 35% by weight. The side crushing strength of the resulting shaped bodies V was 37±2 N. The resulting annular shaped catalyst bodies K3-1 had a side crushing strength of 15 N, an ammonium content (determined by Kjeldahl titration) of 0.53% by weight of $NH_4^+$ and an $MoO_3$ content of 2.1 intensity %.

3. Annular shaped catalyst bodies 3-2 (in process stages B), C), D), F) and G), there was an air atmosphere (27° C. and relative air humidity of 71%))

The production process corresponded to that for preparing the shaped catalyst bodies K3-1, but with the difference that the finely divided aggregate H, before it was recycled upstream of process stage B), had been stored intermediately in an open collecting vessel for 24 hours. In the mixture tabletted with the tabletting machine, the proportion by weight with $d^P \leq 160$ μm was 83% by weight (determination by sieve analysis; lower decomposition and reagglomeration as a result of elevated residual moisture content), with a residual moisture content (a water content) of 6.9% by weight. The weight ratio of residual moisture content to weight loss at 450° C. (heat at 450° C. for 3 h in a porcelain crucible) (which had been calcined to constant weight at 900° C.) under air) was 41%. $G^W$ was 69% by weight. The side crushing strength of the resulting shaped bodies V was 37±2 N. The resulting shaped catalyst bodies K3-2 had a side crushing strength of 15 N, an ammonium content (determined by Kjeldahl titration) of 0.53% by weight of $NH_4^+$ and an $MoO_3$ content of 2.2 intensity %.

VI. Testing of the Annular Catalysts Produced in V. in a Heterogeneously Catalyzed Partial Gas Phase Oxidation of Methacrolein to Methacrylic Acid 2 kg of the particular annular shaped catalyst bodies were charged with an upstream bed and a downstream bed of in each case 50 g of steatite rings (C220 steatite from CeramTec) of geometry 7 mm×7 mm×4 mm (external diameter×length× internal diameter) into a model tubular reactor made of stainless steel (external diameter=30 mm, internal diameter=26 mm, length=4.15 m) (fill height: 397 cm). This was disposed in a nitrogen-sparged salt bath heated to about 287° C. (53% by weight of potassium nitrate, 40% by weight of sodium nitrite and 7% by weight of sodium nitrate). The catalytic testing was effected in cycle gas mode. This resulted in a reactant gas composition (a composition of the starting reaction gas mixture) of approx. 5% by volume of methacrolein, 9% by volume of $O_2$, 17% by volume of steam, 1.5% by volume of CO, 1.8% by volume of $CO_2$ and, as the residual amount of gas to 100% by volume, essentially molecular nitrogen. The mass-based superficial velocity (WHSV) was 0.17 $h^{-1}$.

During the testing, which was for 5 days in each case, the methacrolein conversion $C^{MAC}$ in single pass was kept at approx. 64 mol %. To this end, the salt bath temperature was increased stepwise. The results achieved on the 5th day are shown by table 4 below. In this table, $S^{MAA}$ is the selectivity of methacrylic acid formation, and $S^{COx}$ the selectivity of carbon oxide by-production.

TABLE 4

| Catalyst | $T^S$ (° C.) | $C^{MAC}$ (mol %) | $S^{MAA}$ (mol %) | $S^{COx}$ (mol %) |
|---|---|---|---|---|
| VK3-1 | 293 | 64.0 | 84.1 | 9.9 |
| K3-1 | 291 | 64.4 | 83.8 | 10.1 |
| K3-2 | 293 | 64.4 | 83.1 | 10.6 |

Surprisingly, the inventive recycling in the course of production of the annular catalysts, in the case of $S^{MAA}$, leads only to marginal losses which, with a low residual moisture content (low water content) of the recycled material, and hence a low residual moisture content and a relatively low $G^W$ of the shaped bodies V, vary toward the limit of measurement accuracy.

TABLE 5

| | | 1st belt calciner | | Bed height Belt speed | | | 5.0 cm 2.3 cm/min | | |
| | | 2nd belt calciner | | Bed height Belt speed | | | 10.5 cm 1.0 cm/min | | |

| | | Zone length [cm] | Residence time [min] | Zone temperature [° C.] | Feed air temperature [° C.] | Feed air flow [m³ (STP)/h] | Waste air flow [m³ (STP)/h] | Ventilators [rpm] | NH₃ [% by vol.] |
|---|---|---|---|---|---|---|---|---|---|
| 1st belt calciner | Intake | 50 | 25 | Open, no temperature control | 150 | 35 | | | |
| | Zone 1 | 145 | 72.5 | 164 | 150 | 100 | 70 | 900 | 1.3-1.9 |
| | Zone 2 | 145 | 72.5 | 228 | 150 | 80 | 195 | 500 | 2.3-2.9 |
| | Zone 3 | 145 | 72.5 | 260 | 150 | 115 | 220 | 500 | 0.6-0.9 |
| | Zone 4 | 145 | 72.5 | 286 | 150 | 115 | 240 | 500 | 0.25-0.4 |
| | Transition point to the 2nd belt calciner | 120 | 60 | No temperature control | 150 | 35 | | | |
| 2nd belt calciner | Intake | 125 | 125 | | | 35 | | | |
| | Zone 5 | 145 | 145 | 350 | 320 | 170 | 220 | 500 | 0.14-0.25 |
| | Zone 6 | 145 | 145 | 381 | 320 | 125 | 190 | 500 | 0.05-0.17 |
| | Zone 7 | 145 | 145 | 381 | 320 | 125 | 190 | 500 | |
| | Zone 8 | 145 | 145 | 382 | 320 | 160 | 210 | 500 | |
| | Cooling zone | 200 | 200 | 70 | 320 | 35 | | Switched on | |
| | Outlet | 50 | 50 | | | | | | |
| | Total residence time | | 1330 | | | | | | |

U.S. Provisional Patent Application No. 61/122,129, filed Dec. 12, 2008, is incorporated into the present patent application by literature reference. With regard to the abovementioned teachings, numerous changes and deviations from the present invention are possible. It can therefore be assumed that the invention, within the scope of the appended claims, can be performed differently than the way described specifically herein.

The invention claimed is:
1. A method for heterogeneously catalyzed partial gas phase oxidation of an organic compound, which comprises using, as the catalyst, at least one geometric shaped catalyst body K which comprises as an active material, a multielement oxide which comprises, as elements E other than oxygen, the element Mo, at least one of the two elements Bi and V, and at least one further element from the group consisting of Co, Ni, Fe, Cu and the alkali metals, geometric shaped catalyst body K being obtained by a continuous process having process stages A) to G), in which in process stage A), a finely divided mixture M comprising sources Q of the elements E is prepared with the proviso that at most 10% by weight of the total weight of the particles present in the finely divided mixture M have a particle diameter of $d^M \geq 160$ μm and the particle diameter $d_{50}^M$ of the particles of the finely divided mixture M satisfies the condition 1 μm $\leq d_{50}^M \leq 150$ μm;

in process stage B), the finely divided mixture M*, which consists either only of the finely divided mixture M or of a mixture of the finely divided mixture M and fines F which are obtained in the next process stage C) and are recycled into process stage B) continuously or batchwise from process stage C), is compacted by press agglomeration in which the maximum pressure applied is P1 to agglomerates A whose longest dimension is $\geq 3$ mm;

in process stage C), the agglomerates A are comminuted and the particulate material formed in the comminution is separated by sieving into a powder P whose particle diameters $d^P$ are $\leq 2$ mm and, to an extent of at least 90% by weight, based on the weight of the powder P, $\geq 160$ μm, as sieve oversize, and into fines F as sieve undersize, and the fines F are recycled continuously or batchwise into process stage B to obtain finely divided mixture M*;

in process stage D), the powder P conducted into it or a mixture P* consisting of the powder P conducted into process stage D) and shaping assistants is used to obtain, by press agglomeration in which the maximum pressure applied is P2 and satisfies the relationship P2$\geq$2·P1, geometric shaped bodies V with the proviso that when the powder P is conveyed into process stage D) and when shaping assistants are mixed into the powder P, a particle diameter $d^P \geq 160$ μm is maintained overall in at least 40% by weight of the particles of the powder P, based on the weight thereof; and in process stage E), at least a portion of the shaped bodies V is treated thermally at elevated temperature to obtain the geometric shaped catalyst bodies K, wherein prior to process stage E), the shaped bodies V obtained in process stage D) are separated in an additional separation stage as process stage F) into non-intact shaped bodies V⁻ and into intact shaped bodies V⁺, the shaped bodies V⁺ are fed to process stage E) and in process stage G), non-intact shaped bodies V⁻ are comminuted to form a finely divided aggregate H whose particle diameter $d_{50}^H$ satisfies the condition 1 µm≤$d_{50}^H$≤150 µm and which comprises particles having a particle diameter $d^H$≥160 µm to an extent of at most 10% by weight of its total weight, and the finely divided aggregate H is recycled continuously or batchwise to the additional incorporation into the finely divided mixture M* into process stage B) with the proviso that the content of finely divided aggregate H in the finely divided mixture M*, based on the total weight of the finely divided mixture M*, does not exceed 20% by weight, and wherein $d_{50}^M$ and $d_{50}^H$ are based on volume-based particle diameter distribution determined according to ISO 13320 at a dispersion pressure of 2 bar absolute.

2. The method according to claim 1, wherein the heterogeneously catalyzed partial gas phase oxidation is the partial oxidation of propene to acrolein, of isobutene to methacrolein, of propene to acrylonitrile, of isobutene to methacrylonitrile, of acrolein to acrylic acid or of methacrolein to methacrylic acid.

3. The method according to claim 2, wherein the heterogeneously catalyzed partial gas phase oxidation is the partial oxidation of propene to acrolein.

4. The method according to claim 2, wherein the heterogeneously catalyzed partial gas phase oxidation is the partial oxidation of isobutene to methacrolein.

5. The method according to claim 2, wherein the heterogeneously catalyzed partial gas phase oxidation is the partial oxidation of propene to acrylonitrile.

6. The method according to claim 2, wherein the heterogeneously catalyzed partial gas phase oxidation is the partial oxidation of isobutene to methacrylonitrile.

7. The method according to claim 2, wherein the heterogeneously catalyzed partial gas phase oxidation is the partial oxidation of acrolein to acrylic acid.

8. The method according to claim 2, wherein the heterogeneously catalyzed partial gas phase oxidation is the partial oxidation of methacrolein to methacrylic acid.

* * * * *